United States Patent
Grau-Campistany et al.

(10) Patent No.: US 11,634,458 B2
(45) Date of Patent: Apr. 25, 2023

(54) PEPTIDES AND COMPOSITIONS FOR USE IN COSMETICS AND MEDICINE

(71) Applicant: LIPOTRUE, S.L., Gava (ES)

(72) Inventors: Ariadna Grau-Campistany, Barcelona (ES); Silvia Pastor, Alicante (ES); Patricia Carulla, Barcelona (ES); Juan Carlos Escudero, Barcelona (ES); Julia A. Boras, Castellefels (PL); Isabel Devesa Giner, Elche (ES); Gregorio Fernandez Ballester, Murcia (ES)

(73) Assignee: LIPOTRUE, S.L., Gava (ES)

( * ) Notice: Subject to any disclaimer, the term of this patent is extended or adjusted under 35 U.S.C. 154(b) by 0 days.

(21) Appl. No.: 16/964,890

(22) PCT Filed: Feb. 22, 2019

(86) PCT No.: PCT/EP2019/054479
§ 371 (c)(1),
(2) Date: Jul. 24, 2020

(87) PCT Pub. No.: WO2019/166347
PCT Pub. Date: Sep. 6, 2019

(65) Prior Publication Data
US 2021/0032287 A1 Feb. 4, 2021

(30) Foreign Application Priority Data

Feb. 27, 2018 (EP) .................................... 18382118
Feb. 28, 2018 (EP) .................................... 18382126

(51) Int. Cl.
*A61K 38/00* (2006.01)
*C07K 7/06* (2006.01)
*A61K 8/64* (2006.01)

(52) U.S. Cl.
CPC .................. *C07K 7/06* (2013.01); *A61K 8/64* (2013.01); *A61K 38/00* (2013.01)

(58) Field of Classification Search
CPC ........ C07K 7/06; C07K 5/1019; A61K 38/00; A61K 38/04; A61K 8/64; A61P 21/00; A61P 25/28; A61Q 19/08
See application file for complete search history.

(56) References Cited

U.S. PATENT DOCUMENTS 9,079,048 B2 * 7/2015 Ferrer Montiel ...... A61Q 19/08

FOREIGN PATENT DOCUMENTS

| WO | 9921879 A1 | 5/1999 |
| WO | 2006050930 A2 | 5/2006 |
| WO | WO-2014081845 A2 * | 5/2014 | ............. A61K 38/06 |

OTHER PUBLICATIONS

Fulop et al. Aging, frailty and age-related diseases. Biogerontology (2010) 11:547-563 (Year: 2010).*
Kim et al. Study of Preventing Methods for Skin Aging and Wrinkle. Korean J. Oriental Physiology & Pathology 24(4):533~542, 2010 (Year: 2010).*
Harman Denham. The aging process. Proc. Natl Acad. Sci. USA vol. 78, No. 11, pp. 7124-7128, Nov. 1981 . (Year: 1981).*
Payza et al., "Neuropeptide FF receptors: structure-activity relationship and effect of morphine", Journal of Pharmacology and Experimental Therapeutics, 1993, vol. 267, No. 1, pp. 88-94.
Brussaard et al., "One Receptor Type Mediates Two Independent Effects of FMRFa on Neurosecretory Cells of Lymnaea", Peptides, 1989, vol. 10, pp. 289-297.
Blanes-Mira et al., "A Synthetic Hexapeptide (Argireline) With Antiwrinkle Activity", International Journal of Cosmetic Science, 2002,vol. 24, No. 5, pp. 303-310.
International Search Report and Written Opinion for Corresponding International Application No. PCT/EP2019/054479 (dated Jun. 18, 2019) (13 Pages).

* cited by examiner

*Primary Examiner* — Aradhana Sasan
*Assistant Examiner* — Mercy H Sabila
(74) *Attorney, Agent, or Firm* — Lucas & Mercanti, LLP

(57) ABSTRACT

The present invention relates to a family of peptides which are able to interfere in the formation of complex Munc18-Syntaxin-1 and, hence, are useful in the prevention and/or treatment of neuronal exocytosis and/or muscle contractility disorders; and to prevent, reduce and/or eliminate skin aging and/or expression signs.

Figure 1A:
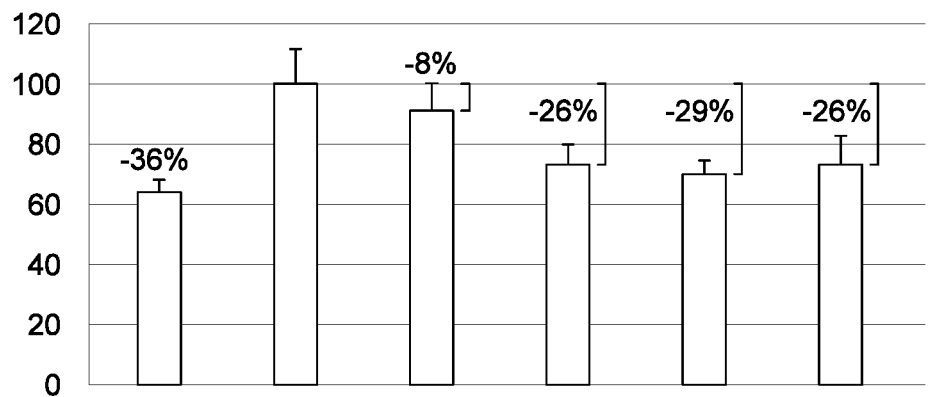
Figure 1B:
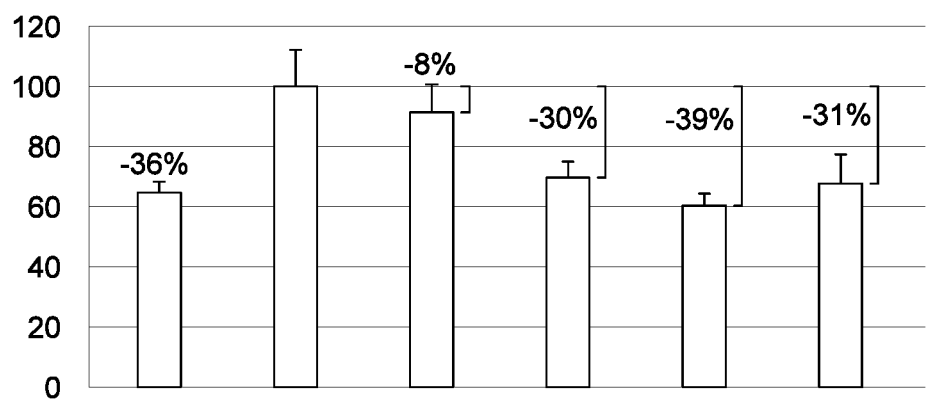
Figure 1C:
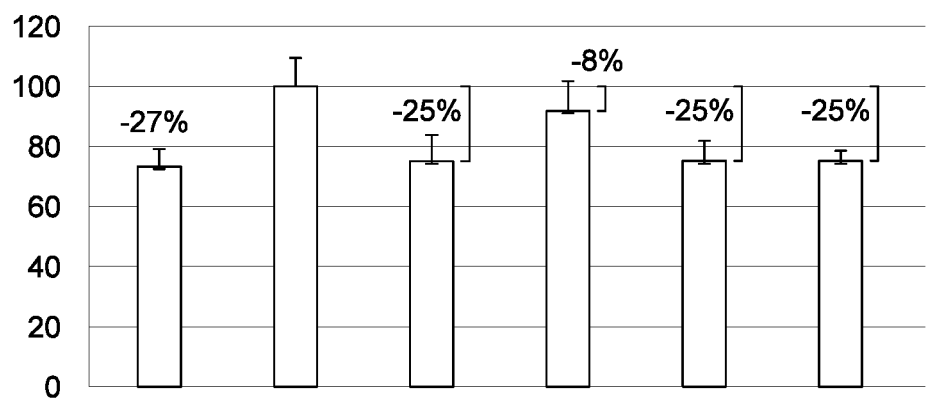
Figure 1D:
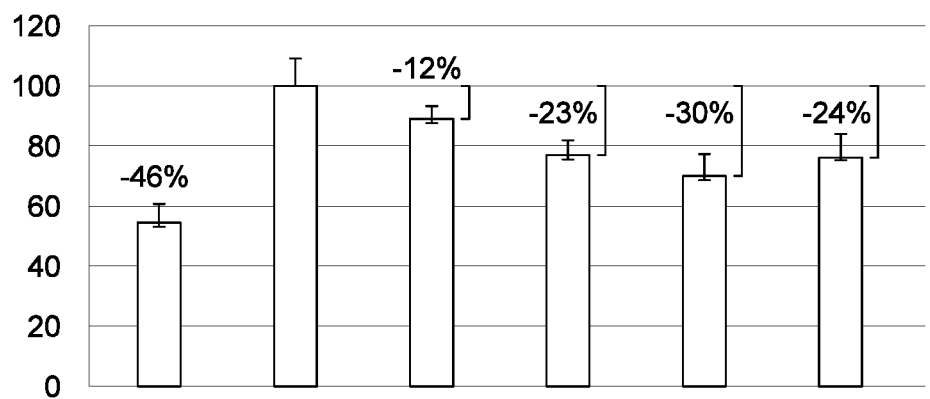
Figure 1E:
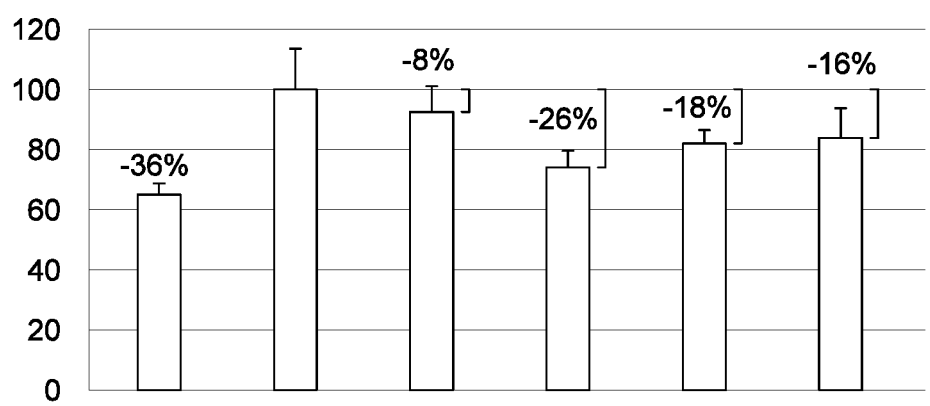
Figure 1F:
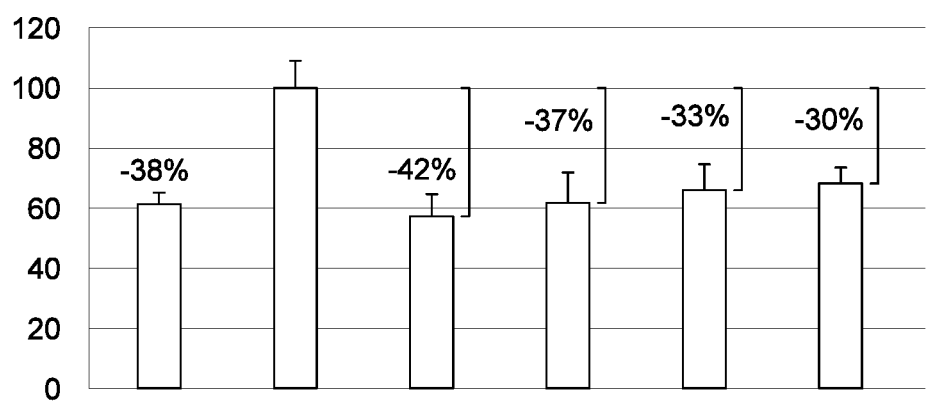
Figure 1G:
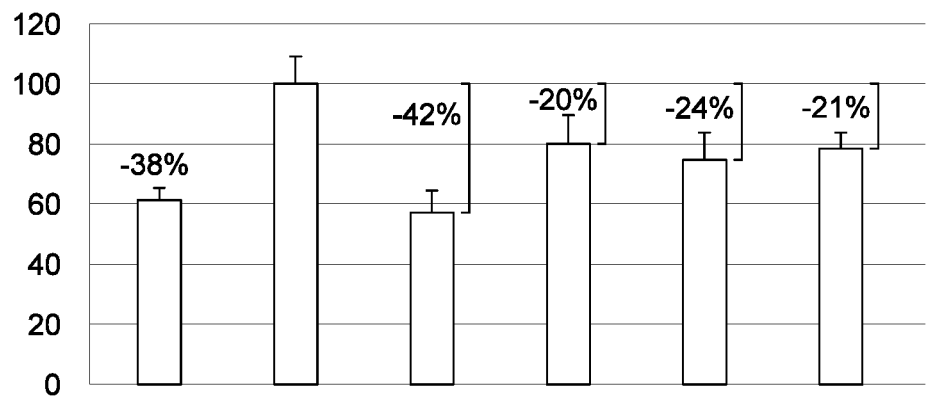
Figure 1H:
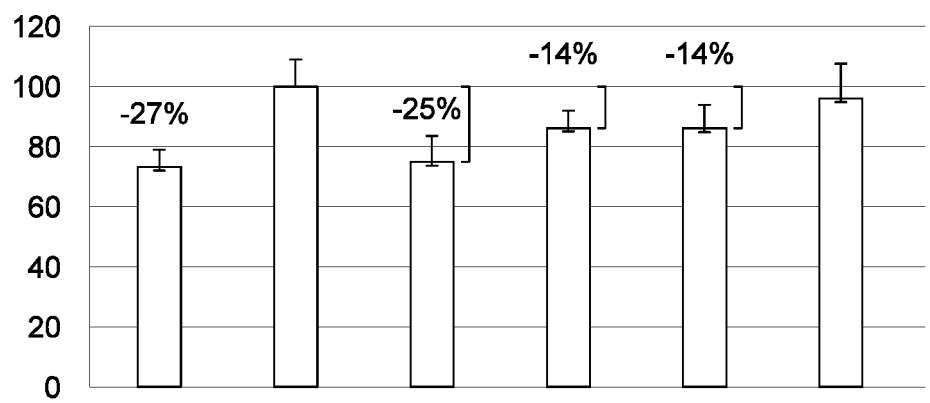
Figure 1I:
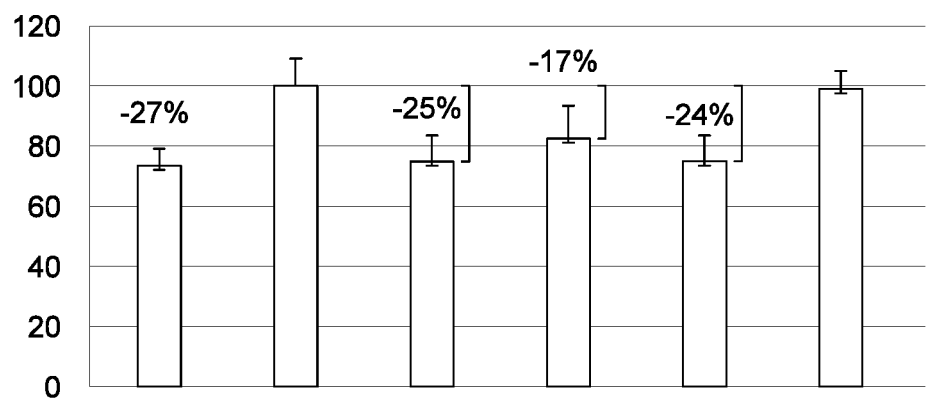

24 Claims, 14 Drawing Sheets
Specification includes a Sequence Listing.

PEPTIDES AND COMPOSITIONS FOR USE IN COSMETICS AND MEDICINE

CROSS REFERENCE TO RELATED APPLICATION

This Application is a 371 of PCT/EP2019/054479, filed Feb. 22, 2019, which claims the benefit of European Patent Application Nos. 18382118.0, filed Feb. 27, 2018 and 18382126.3, filed Feb. 28, 2018, each of which are incorporated herein by reference.

The present invention relates to the field of molecular biology, more precisely to molecular biology applied to cosmetics and medicine, even more precisely to peptides and compositions comprising said peptides, able to modulate the binding or interaction between Munc18 and Syntaxin-1 and, hence, the binding of the SNARE complex. Due to this activity, the peptides and compositions of the present invention are able to modulate synaptic vesicle fusion and muscle contractility. Therefore, said peptides and compositions are effective in the treatment of conditions related with the modulation of the above-mentioned aspects (for example, muscle relaxation) and are useful both in cosmetics (anti-wrinkling activity and activity against hyperhidrosis) and in medicine (neuronal and/or muscle contraction disorders).

Abnormal modulation of the SNARE complex and of synaptic vesicle fusion leads, among others, to an abnormal muscular contraction-relaxation which is known to be very relevant in both, cosmetics and medicine.

On the one side, wrinkle (for example, facial expression wrinkles) formation basis or mechanism is a tension of muscles dragging the skin inwardly. This muscular tension is the result of an hyperactivity of the nerves enervating the corresponding muscles. Said nervous hyperactivity is, in turn, characterized by an uncontrolled and excessive release of neurotransmitters exciting muscular fibers.

On the other side, nervous hyperactivity (characterized, as already noted above, by an uncontrolled and excessive release of neurotransmitters exciting muscular fibers) which leads to an alteration of muscular contraction-relaxation is also at the basis of several known diseases, for example, senile dementia, Alzheimer's-related dementia, AIDS-related dementia, epilepsy, amiotrophic sclerosis or multiple/lateral sclerosis (Jabbari B, (2018) *Botulinum Toxin Treatment in Clinical Medicine A Disease-Oriented Approach*, Springer, Cham; Jankovic J, (2004) *Botulinum toxin in clinical practice, J Neurol Neurosurg Psychiatry,* 75:951-957)

In a similar way as stated above, abnormalities in the SNARE complex and in synaptic vesicle fusion which leads to a dysregulation of neuronal exocytosis cannot only produce an excessive activation or excitation of muscle but also of other structures or organs such as, for example, glands. Therefore, said conditions also lead to cosmetic and medical alterations (for which the peptides and compositions of the present invention are useful) not related with muscular contraction as, for example, hyperhidrosis (excessive activation or excitation of sweat glands) (Jabbari B, (2018) *Botulinum* Toxin *Treatment in Clinical Medicine A Disease-Oriented Approach, Springer, Cham.*; Luvisetto S, Gazerani P, Cianchetti C, Pavone F, (2015) *Botulinum* Toxin *Type A as a Therapeutic Agent against Headache and Related Disorders*, Toxins (Basel), September; 7(9): 3818-3844; Molderings G J, Haenisch B, Brettner S, et.al., (2016) *Pharmacological treatment options for mast cell activation disease*, Arch Pharmacol. 2016; 389: 671-694.; Başar E, Arici C, (2016), *Use of Botulinum Neurotoxin in Ophthalmology*, Turk J Ophthalmol. December; 46(6): 282-290.; Schlereth T, Dieterich M, Birklein F (2009), *Hyperhidrosis—causes and treatment of enhanced sweating*, Dtsch Arztebl Int. January; 106(3):32-7).

Neurotransmitter release is due to presynaptic vesicle fusion, which, as it is widely known is controlled by complex interactions between different proteins which are in charge of approximating the vesicles with the neurotransmitter to the presynaptic membrane, positioning said vesicle for its secretion, allowing the fusion of the membranes for the secretion and disassembling the generated complex to allow its recycling. All this procedure, including the assembly and disassembly of the participating proteins, needs to be tightly controlled as any type of dysregulation may lead to alterations, with both, aesthetical and/or health effects.

Molecules regulating neuronal exocytosis contribute to relaxing muscular tension and, therefore, to prevent, decrease and/or eliminate wrinkles (preferably, facial wrinkles) and/or prevent, ameliorate or cure diseases related with abnormal or dysregulated neuronal exocytosis.

In this connection, it has traditionally been considered that presynaptic vesicle (loaded with neurotransmitter, preferably, acetylcholine) fusion was driven or controlled by SNARE proteins (this is, syntaxin-1 and SNAP-25 in the membrane of the neurone; and synaptobrevin or VAMP in the membrane of the vesicle). Therefore, it was considered that the SNARE protein complex formed a key target for controlling neurosecretion.

In this connection several therapeutic and cosmetic approaches directed against the SNARE protein complex have been generated, as, for example:

Botulinum toxins: they have been widely used with the aim of reducing and/or eliminating expression wrinkles, especially serotype A (BOTOX® Cosmetic, Allergan Inc.). Said botulinum toxins are injected locally and their paralytic effects are reversible with an average duration of 6 months requiring, hence, repeated injections. It is known the risk of triggering an immune reaction against the botulinum preparation leading to a loss of the treatment efficacy. Other serotypes of botulinum toxins, such as B, F and E, have also been considered to overcome this problem, however, said serotypes also have the risk of triggering an immune response. At a molecular level, botulinum toxins are proteases degrading neuronal proteins that are involved in the calcium ion-activated exocytosis mechanism. For example, botulinum toxin A, truncates the neuronal SNAP-25 protein.

It is also known in the state of the art that certain peptides derived from the sequences of the proteins forming the SNARE complex can inhibit neuronal exocytosis, such as, for example: peptides derived from the amino and carboxyl domains of the SNAP-25 (see, for example, PCT Patent application WO97/34620, European Patent EP1180524B1 and European Patent EP2123673B1) and peptides derived from synaptobrevin or from syntaxin (see, for example, PCT Patent application WO97/34620; Blanes-Mira, C., Clemente, J., Jodas, G., Gil, A., Fernandez-Ballester, G., Ponsati, B., Gutierrez, L., Perez-Paya, E., Ferrer-Montiel, A. *A synthetic hexapeptide (Argireline) with antiwrinkle activity*. International Journal of Cosmetic Science, (2002), 24, 303-310).

However, there is still the need to find additional or alternative molecules which interfere in the mechanisms of synaptic neurotransmitter release and allow its inhibition, allowing the inhibition of neuronal exocytosis and, hence, providing for, among other, muscular relaxation or depletion of gland hyperstimulation and the corresponding cosmetic and pharmaceutical effects.

Recent studies have suggested a more complex regulation of synaptic neurotransmitter release in which, in addition to the SNARE protein complex, other proteins, such as Munc13 and Munc18, would have an important role both in the regulation of the procedure and in allowing the fusion of the membranes (Rizo, J and Südhof, T. C. (2012) *The Membrane Fusion Enigma: SNAREs, Sec1/Munc18 Proteins, and Their Accomplices—Guilty as Charged?*; Annu. Rev. Cell Dev. Biol., 28:279-308). In this sense, the interaction between Munc18 (SEQ ID NO: 1) and Syntaxin-1 (SEQ ID NO: 2) has been described as central and essential, both for the generation of the SNARE complex and for the fusion of the membranes. On the one side, Munc18 interacts with $H_{abc}$-domain of Syntaxin-1 allowing stabilization of said Munc18 and its appropriate trafficking. On the other side, the interaction of Munc18 with the N peptide of Syntaxin-1 is necessary for the interaction of Munc18 with the SNARE complex and for the fusion of the membranes (Zhou, P. et.al. (2013) *Syntaxin-1 N-peptide and Habc-domain perform distinct essential functions in synaptic vesicle fusion*; The EMBO Journal, 32:159-171; Rizo, J and Südhof, T. C. (2012) *The Membrane Fusion Enigma: SNAREs, Sec1/Munc18 Proteins, and Their Accomplices—Guilty as Charged?*; Annu. Rev. Cell Dev. Biol., 28:279-308).

The inventors of the present invention, after extensive and exhaustive research, have surprisingly found that peptides competing with specific sequences located in the surface of interaction between Munc18 and Syntaxin-1 allow an interference or inhibition of said complex Munc18-Syntaxin-1 and, hence an inhibition of neurotransmitter release (preferably, acetylcholine and CGRP (Calcitonin gene-related peptide)) and an inhibition of muscular contraction (both, indirectly by means of inhibition of neuronal exocytosis, and also by providing an effect directly in muscle cells). It has surprisingly been found that peptides competing with other sequences located in the surface of interaction between Munc18 and Syntaxin-1 do not provide for the above-mentioned effects. Therefore, the inventors of the present invention have found that peptides competing with SEQ ID NO: 3 (corresponding to positions 46 to 51 of Munc18, this is, of SEQ ID NO: 1) and/or SEQ ID NO: 4 (corresponding to positions 63 to 66 of Munc18, this is, of SEQ ID NO: 1), both of Munc18, are advantageous over other sequences located in the surface of interaction between Munc18 and Syntaxin-1 for the interference of the interaction between Munc18 and Syntaxin-1. Said peptides (the peptides of the present invention) have shown an effective interference of the interaction between Munc18 and Syntaxin-1. Additionally, these peptides have shown a direct muscle relaxant effect, as they have the ability to act directly on muscle cells, that is, on the post-synaptic side by modulating genes involved in the muscle contraction and modulating calcium mobilization, as seen for other peptides (Schagen, S. K. (2017) *Topical treatments with effective anti-aging results*, Cosmetics, 4, 16; PCT Patent application WO2006047900). Hence, have shown an effect both in the presynaptic side and in the postsynaptic side by allowing an effective inhibition of acetylcholine release in neurons, and a modulation of gene expression and reduction of calcium mobilization on muscle cells. Therefore, the peptides of the present invention solve the above-mentioned problem and are useful for the treatment of both, cosmetic signs and diseases related with dysregulation of neuronal exocytosis and/or muscle contractility.

The inventors are not aware of any prior art which provides for molecules interfering in the interaction between Munc18 and Syntaxin-1 to inhibit neurotransmitter release (and, therefore, inhibit neuronal exocytosis) and muscle contractility.

In a first aspect, the present invention refers to a peptide capable of interfering in the Munc18-Syntaxin-1 complex interaction by competing with specific regions of the surface of interaction between Munc18 and Syntaxin-1. More precisely, the peptides of the present invention compete with SEQ ID NO: 3 and/or SEQ ID NO:4, both sequences being located in Munc18, in its surface of interaction with Syntaxin-1.

In a second aspect, the present invention refers to a composition comprising a peptide of the present invention (one peptide of the present invention or a combination thereof).

In a further aspect, the present invention refers to a composition or peptide of the present invention for use as a medicament, more precisely for use in the prevention, amelioration and/or treatment of neuronal exocytosis and/or muscle contractility disorders, even more precisely for use in the prevention, amelioration and/or treatment of diseases associated with a dysregulation of SNARE complex formation, dysregulation of striated muscle contraction, dysregulation of acetylcholine and/or CGRP release and/or dysregulation of $Ca^{2+}$ channel activation.

In a forth aspect, the present invention refers to a method for the prevention, amelioration and/or treatment of neuronal exocytosis and/or muscle contractility disorders, even more precisely for the prevention, amelioration and/or treatment of a disease associated with a dysregulation of SNARE complex formation, dysregulation of striated muscle contraction, dysregulation of acetylcholine and/or CGRP release and/or dysregulation of $Ca^{2+}$ channel activation, comprising administering a peptide or a composition of the present invention to a subject in need thereof.

Furthermore, the present invention in a fifth aspect refers to the use as a cosmetic of a peptide or a composition of the present invention to prevent, reduce and/or eliminate cosmetic signs related with dysregulation of neuronal exocytosis and/or of muscle contractility in a subject, more specifically, skin aging or expression signs.

In a sixth aspect, the present invention refers to the cosmetic use of a peptide or a composition of the present invention to prevent, reduce and/or eliminate cosmetic signs related with dysregulation of neuronal exocytosis and/or of muscle contractility in a subject, more specifically, skin aging or expression signs.

In a seventh aspect, the present invention refers to a method to prevent, reduce and/or eliminate cosmetic signs related with dysregulation of neuronal exocytosis and/or of muscle contractility (more specifically, skin aging or expression signs) in a subject in need thereof, characterized in that it comprises the use of a peptide or a composition of the present invention.

The term "non-cyclic aliphatic group" and its plural, as used herein, have the common meaning given in the state of the art to said terms. Therefore, these terms refer to, for example and not restricted to, linear or branched alkyl, alkenyl and alkynyl groups.

The term "alkyl group" and its plural, as used herein, refer to a saturated, linear or branched group, which has between 1 and 24, preferably between 1 and 16, more preferably between 1 and 14, even more preferably between 1 and 12, and even more preferably still between 1, 2, 3, 4, 5 or 6 carbon atoms and which is bound to the rest of the molecule by a simple bond, including, for example and not restricted to, methyl, ethyl, isopropyl, n-propyl, i-propyl, isobutyl, tert-butyl, n-butyl, sec-butyl, n-pentyl, n-hexyl, heptyl, octyl, decyl, dodecyl, lauryl, hexadecyl, octadecyl, amyl, 2-ethylhexyl, 2-methylbutyl, 5-methylhexyl and similar. The alkyl groups can be optionally substituted by one or more substituents, such as, halo, hydroxy, alkoxy, carboxy, carbonyl, cyano, acyl, alkoxy-carbonyl, amino, nitro, mercapto and alkoxythio.

The term "alkenyl group" and its plural, as used herein, refer to a linear or branched group which has between 2 and 24, preferably between 2 and 16, more preferably between 2 and 14, even more preferably between 2 and 12, even more preferably still 2, 3, 4, 5 or 6 carbon atoms, with one or more carbon-carbon double bonds, preferably with 1, 2 or 3 carbon-carbon double bonds, conjugated or unconjugated, which is bound to the rest of the molecule through a single bond, including, for example and not restricted to, the vinyl, oleyl, linoleyl and similar groups. The alkenyl groups can be optionally substituted by one or more substituents, such as, halo, hydroxy, alkoxy, carboxy, carbonyl, cyano, acyl, alkoxy-carbonyl, amino, nitro, mercapto and alkoxythio.

The term "alkynyl group" and its plural, as used herein, refer to a linear or branched group which has between 2 and 24, preferably between 2 and 16, more preferably between 2 and 14, even more preferably between 2 and 12, even more preferably still 2, 3, 4, 5 or 6 carbon atoms, with one or more carbon-carbon triple bonds, preferably with 1, 2 or 3 carbon-carbon triple bonds, conjugated or unconjugated, which is bound to the rest of the molecule through a single bond, including, for example and not restricted to, the ethinyl group, 1-propinyl, 2-propinyl, 1-butinyl, 2-butinyl, 3-butinyl, pentinyl, such as 1-pentinyl and similar groups. The alkynyl groups can be optionally substituted by one or more substituents, such as, halo, hydroxy, alkoxy, carboxy, carbonyl, cyano, acyl, alkoxy-carbonyl, amino, nitro, mercapto and alkoxythio.

The term "alicyclic group" and its plural, as used herein, have the common meaning given in the state of the art to said terms. Hence, these terms are used to refer to, for example and not restricted to, cycloalkyl or cycloalkenyl or cycloalkynyl groups.

The term "cycloalkyl" and its plural, as used herein, refer to a saturated mono- or polycyclic aliphatic group which has between 3 and 24, preferably between 3 and 16, more preferably between 3 and 14, even more preferably between 3 and 12, even more preferably still 3, 4, 5 or 6 carbon atoms and which is bound to the rest of the molecule through a single bond, including, for example and not limited to, cyclopropyl, cyclobutyl, cyclopentyl, cyclohexyl, cycloheptyl, methyl cyclohexyl, dimethyl cyclohexyl, octahydroindene, decahydronaphthalene, dodecahydro-phenalene, adamantyl and similar, and that can optionally be substituted by one or more groups, such as, alkyl, halo, hydroxy, alkoxy, carboxy, carbonyl, cyano, acyl, alkoxy-carbonyl, amino, nitro, mercapto and alkoxythio.

The term "cycloalkenyl" and its plural, as used herein, refer to a non-aromatic mono- or polycyclic aliphatic group which has between 5 and 24, preferably between 5 and 16, more preferably between 5 and 14, even more preferably between 5 and 12, even more preferably still 5 or 6 carbon atoms, with one or more carbon-carbon double bonds, preferably with 1, 2 or 3 carbon-carbon double bonds, conjugated or unconjugated, which is bound to the rest of the molecule through a single bond, including, for example and not restricted to, the cyclopent-1-en-1-yl group and similar groups, and that can optionally be substituted by one or more groups, such as, alkyl, halo, hydroxy, alkoxy, carboxy, carbonyl, cyano, acyl, alkoxy-carbonyl, amino, nitro, mercapto and alkoxythio.

The term "cycloalkynyl" and its plural, as used herein, refer to a non-aromatic mono- or polycyclic aliphatic group which has between 8 and 24, preferably between 8 and 16, more preferably between 8 and 14, even more preferably between 8 and 12, even more preferably still 8 or 9 carbon atoms, with one or more carbon-carbon triple bonds, preferably with 1, 2 or 3 carbon-carbon triple bonds, conjugated or unconjugated, which is bound to the rest of the molecule through a single bond, including, for example and not restricted to, the cyclooct-2-yn-1-yl group and similar, and that can optionally be substituted by one or more groups, such as, alkyl, halo, hydroxy, alkoxy, carboxy, carbonyl, cyano, acyl, alkoxy-carbonyl, amino, nitro, mercapto and alkoxythio.

The term "aryl group" and its plural, as used herein, refer to an aromatic group which has between 6 and 30, preferably between 6 and 18, more preferably between 6 and 10, even more preferably 6 or 10 carbon atoms, which comprises 1, 2, 3 or 4 aromatic rings, bound by a carbon-carbon bond or fused, and which is bound to the rest of the molecule through a single bond, including, for example and not restricted to, phenyl, naphthyl, diphenyl, indenyl, phenanthryl or anthranyl among others. The aryl group can be optionally substituted by one or more substituents, such as, halo, hydroxy, alkoxy, carboxy, carbonyl, cyano, acyl, alkoxy-carbonyl, amino, nitro, mercapto and alkoxythio.

The term "aralkyl group" and its plural, as used herein, refer to an alkyl group substituted by an aromatic group, with between 7 and 24 carbon atoms and including, for example and not restricted to, —($CH_2$)1-6-phenyl, —($CH_2$)1-6-(1-naphtyl), —($CH_2$)1-6-(2-naphtyl), —($CH_2$)1-6-CH(phenyl)$_2$ and similar. The aralkyl groups can be optionally substituted by one or more substituents, such as, halo, hydroxy, alkoxy, carboxy, carbonyl, cyano, acyl, alkoxy-carbonyl, amino, nitro, mercapto and alkoxythio.

The term "heterocyclic group" and its plural, as used herein, refer to a 3-10 member heterocycyl or hydrocarbon ring, in which one or more of the ring atoms, preferably 1, 2 or 3 of the ring atoms, is a different element to carbon, such as nitrogen, oxygen or sulfur and may be saturated or unsaturated. For the purposes of this invention, the heterocyclyl can be a cyclic, monocyclic, bicyclic or tricyclic system which may include fused ring systems; and the nitrogen, carbon or sulfur atoms can be optionally oxidized in the heterocyclyl radical; the nitrogen atom can optionally be quaternized; and the heterocyclyl radical may be partially or completely saturated or may be aromatic. With increasing preference, the term heterocyclic relates to a 5 or 6-member ring. The heterocyclic groups can be optionally substituted by one or more substituents, such as, halo, hydroxy, alkoxy, carboxy, carbonyl, cyano, acyl, alkoxy-carbonyl, amino, nitro, mercapto and alkoxythio.

The term "heteroarylalkyl group" and its plural, as used herein, refer to an alkyl group substituted with a substituted or unsubstituted aromatic heterocyclyl group, the alkyl group having from 1 to 6 carbon atoms and the aromatic heterocyclyl group between 2 and 24 carbon atoms and from 1 to 3 atoms other than carbon and including, for example and not restricted to, —($CH_2$)1-6-imidazolyl, —($CH_2$)1-6-triazolyl, —($CH_2$)1-6-thienyl, —($CH_2$)1-6-furyl, —($CH_2$)1-6-pyrrolidinyl and similar. The heteroarylalkyl groups can be optionally substituted by one or more substituents, such as, halo, hydroxy, alkoxy, carboxy, carbonyl, cyano, acyl, alkoxy-carbonyl, amino, nitro, mercapto and alkoxythio.

The terms "halo" or "halogen", as used in the present document, refer to fluorine, chlorine, bromine or iodine, and its anions are referred to as halides.

As used herein, the term "derivative" and its plural, refer both to cosmetically acceptable compounds, this is, derived from the compound of interest that can be used in the preparation of a cosmetic, and to cosmetically unacceptable derivatives since these may be useful in the preparation of cosmetically acceptable derivatives. The term "derivative" and its plural also refer to both, pharmaceutically acceptable compounds, this is, derived from the compound of interest that can be used in the preparation of a medicament, and to pharmaceutically unacceptable derivatives since these may be useful in the preparation of pharmaceutically acceptable derivatives.

As used in the present document, the term "salt" and its plurals refer to any type of salt from among those known in the state of the art, for example, halide salts, hydroxy acid salts (such as oxyacid salts, acid salts, basic salts and double salts), hydroxo salts, mixed salts, oxy salts or other hydrated salts. This term comprises both cosmetically and/or pharmaceutically acceptable salts and cosmetically and/or pharmaceutically unacceptable salts, since the latter may be useful in the preparation of cosmetically and/or pharmaceutically acceptable salts.

As used in the present document, the term "isomer" and its plural refer to optical isomers, enantiomers, stereoisomers or diastereoisomers. The individual enantiomers or diastereoisomers, as well as their mixtures, may be separated by conventional techniques known in the state of the art.

As used herein, the term "solvate" and its plural refer to any solvate known in the state of the art, such as polar, apolar or amphiphilic solvates, and include any cosmetically acceptable solvate which, when administered or applied to the interested subject (directly or indirectly) provides the compound of interest (the peptide or peptides of the present invention). Preferably, the solvate is a hydrate, a solvate with an alcohol such as methanol, ethanol, propanol or isopropanol, a solvate with an ester such as ethyl acetate, a solvate with an ether such as methyl ether, ethyl ether or THE (tetrahydrofuran) or a solvate with DMF (dimethylformamide), and more preferably a hydrate or a solvate with an alcohol such as ethanol.

In addition, as used herein, the term "amino acid" and its plural include the amino acids codified by the genetic code as well as uncodified amino acids, whether they are natural or not and whether they are D- and L-amino acids. Examples of uncodified amino acids are, without restriction, citrulline, ornithine, sarcosine, desmosine, norvaline, 4-aminobutyric acid, 2-aminobutyric acid, 2-aminoisobutyric acid, 6-aminohexanoic acid, 1-naphthylalanine, 2-naphthylalanine, 2-aminobenzoic acid, 4 aminobenzoic acid, 4-chlorophenylalanine, 2,3-diaminopropionic acid, 2,4 diaminobutyric acid, cycloserine, carnitine, cysteine, penicillamine, pyroglutamic acid, thienylalanine, hydroxyproline, allo-isoleucine, allo-threonine, isonipecotic acid, isoserine, phenylglycine, statin, β-alanine, norleucine, N-methylamino acids, α-amino acids and β-amino acids, among others, as well as their derivatives. Nevertheless, further unnatural amino acids are known in the state of the art (see, for example, "*Unusual amino acids in peptide synthesis*" by D. C. Roberts and F. Vellaccio, The Peptides, Vol. 5 (1983), Chapter VI, Gross E. and Meienhofer J., Eds., Academic Press, New York, USA).

As used herein, "expression wrinkles" are the wrinkles resulting from the stress exerted by the contractions of facial muscles responsible for causing facial expressions on the skin of the face. Said wrinkles are usually located on the forehead, in the space between the eyebrows, around the mouth and/or around the eyes.

As stated previously, in a first aspect, the present invention refers to a peptide capable of interfering in the Munc18-Syntaxin-1 complex interaction characterized in that it competes with SEQ ID NO: 3 and/or SEQ ID NO:4, its acceptable isomers, salts, solvates and/or derivatives and/or mixtures thereof.

It is contemplated that the amino acids used or present in the peptides of the present invention are L-amino acids, D-amino acids or combinations thereof. In a preferred embodiment, the amino acids used or present in the peptides of the present invention are L-amino acids.

Preferably, the isomers mentioned above are stereoisomers. It is contemplated that said stereoisomers are enantiomers or diastereoisomers. Hence, in a preferred embodiment of the present invention, the peptide is a racemic mixture, a diastereomeric mixture, a pure enantiomer or a pure diastereoisomer.

It is contemplated that the peptide of the present invention comprises at least one moiety bound at its N-terminus and/or at its C-terminus. Said at least one moiety may be bound to the peptide by any means known in the state of the art, preferably covalently. In a preferred embodiment, the peptide comprises one moiety bound covalently to its N-terminus and one moiety bound covalently to its C-terminus.

In an embodiment, the at least one N-terminus moiety (preferably, one N-terminus moiety) is selected from H, substituted or unsubstituted non-cyclic aliphatic, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO— wherein $R_5$ is selected from the group formed by substituted or unsubstituted $C_1$-$C_{24}$ alkyl radical, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_3$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl ring of 3 to 10 members, and substituted or unsubstituted heteroarylalkyl of 2 to 24 carbon atoms and 1 to 3 atoms other than carbon and an alkyl chain of 1 to 6 carbon atoms. More preferably, the at least one N-terminus moiety (preferably, one N-terminus moiety) is selected from H or $R_5$—CO—, wherein $R_5$ is selected from the group formed by substituted or unsubstituted $C_1$-$C_{24}$ alkyl radical, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_3$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl ring of 3 to 10 members, and substituted or unsubstituted heteroarylalkyl of 2 to 24 carbon atoms and 1 to 3 atoms other than carbon and an alkyl chain of 1 to 6 carbon atoms. Even more preferably, the at least one N-terminus moiety (preferably, one N-terminus moiety) is selected from H, acetyl (hereinafter, Ac), tert-butanoyl, hexanoyl, 2-methylhexanoyl, cyclohexanecarboxyl, octanoyl, decanoyl, lauroyl myristoyl, palmitoyl (hereinafter, Pal), stearoyl, oleoyl and linoleoyl. In the most preferred embodiment, the at least one N-terminus moiety (preferably, one N-terminus moiety) is Ac.

In an embodiment, the at least one C-terminus moiety (preferably, one C-terminus moiety) is selected from is selected from H, —$NR_3R_4$—, —$OR_3$ and —$SR_3$, wherein $R_3$ and $R_4$ are independently selected from H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl. In the most preferred embodiment, the at least one C-terminus moiety (preferably, one C-terminus moiety) is $NH_2$.

Therefore, more preferably, the peptide of the present invention comprises one moiety bound to the N-terminus and one moiety bound to the C-terminus, wherein the moiety bound to the N-terminus is Ac and the moiety bound to the C-terminus is $NH_2$.

In an embodiment, the sequence of the peptide of the present invention is SEQ ID NO: 3 or SEQ ID NO:4 (as stated above, said peptide can comprise at least one moiety bound to is N-terminus and/or at least one moiety bound to its C-terminus, more preferably it comprises one moiety bound to the N-terminus and one moiety bound to the C-terminus, wherein the moiety bound to the N-terminus is Ac and the moiety bound to the C-terminus is $NH_2$). It is contemplated that a peptide of the present invention has a sequence with at least a 70% identity with SEQ ID NO: 3 or SEQ ID NO:4, even more preferably, an 80% identity with SEQ ID NO: 3 or SEQ ID NO:4, even more preferably, a 90% identity with SEQ ID NO: 3 or SEQ ID NO:4, even more preferably, a 95% identity with SEQ ID NO: 3 or SEQ ID NO:4; and even more preferably, a 99% identity with SEQ ID NO: 3 or SEQ ID NO:4.

In one of the preferred embodiments, the sequence of a peptide of the present invention is in accordance with formula (I):

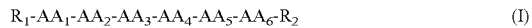

$$R_1\text{-}AA_1\text{-}AA_2\text{-}AA_3\text{-}AA_4\text{-}AA_5\text{-}AA_6\text{-}R_2 \quad (I)$$

their cosmetically and pharmaceutically acceptable isomers, salts, solvates and/or derivatives and mixtures thereof, wherein:
$AA_1$ is selected from the group of amino acids with positively charged side-chain or polar not charged side-chain;
$AA_2$ is selected from the group of amino acids with non-polar hydrophobic side-chain;
$AA_3$ is selected from the group of amino acids with non-polar hydrophobic side-chain;
$AA_4$ is selected from the group of amino acids with charged side-chain;
$AA_5$ is selected from the group of amino acids with non-polar hydrophobic side-chain or aromatic side-chain;
$AA_6$ is Trp;
$R_1$ is selected from H, substituted or unsubstituted non-cyclic aliphatic, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO— wherein $R_5$ is selected from the group formed by substituted or unsubstituted $C_1$-$C_{24}$ alkyl radical, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_3$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl ring of 3 to 10 members, and substituted or unsubstituted heteroarylalkyl of 2 to 24 carbon atoms and 1 to 3 atoms other than carbon and an alkyl chain of 1 to 6 carbon atoms; and $R_2$ is selected from H, —$NR_3R_4$—, —$OR_3$ and —$SR_3$, wherein $R_3$ and $R_4$ are independently selected from H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl.

More preferably, in this preferred embodiment, in formula (I):
$AA_1$ is His;
$AA_2$ is selected from the group of amino acids with non-polar hydrophobic side-chain;
$AA_3$ is selected from the group of amino acids with non-polar hydrophobic side-chain;
$AA_4$ is selected from the group of amino acids with charged side-chain;
$AA_5$ is selected from Met or the group of amino acids with aromatic side-chain; and
$AA_6$ is Trp.

More preferably, in this preferred embodiment, in formula (I):
$AA_1$ is His;
$AA_2$ is selected from the group of Gly, Ala, Val, Leu, Met and Ile;
$AA_3$ is selected from the group of Gly, Ala, Val, Leu, Met and Ile;
$AA_4$ is selected from the group of Lys, Arg, His, Asp and Glu;
$AA_5$ is selected from the group of Met, Phe, Tyr and Trp; and
$AA_6$ is Trp.

More preferably, in this preferred embodiment, in formula (I):
$AA_1$ is His;
$AA_2$ is selected from the group of Ala and Ile;
$AA_3$ is selected from the group of Leu and Met;
$AA_4$ is selected from the group of Arg and Asp;
$AA_5$ is selected from the group of Met, Phe and Trp; and
$AA_6$ is Trp.

Even more preferably, in this preferred embodiment, the sequence of a peptide in accordance with the present invention is:

$$R_1\text{-His-Ile-Leu-Asp-Met-Trp-}R_2; \quad (R_1\text{-SEQ ID NO: 5-}R_2)$$

$$R_1\text{-His-Ile-Met-Asp-Phe-Trp-}R_2; \quad (R_1\text{-SEQ ID NO: 6-}R_2)$$

$$R_1\text{-His-Ile-Leu-Asp-Trp-Trp-}R_2; \quad (R_1\text{-SEQ ID NO: 7-}R_2)$$

$$R_1\text{-His-Ala-Leu-Arg-Phe-Trp-}R_2; \quad (R_1\text{-SEQ ID NO: 8-}R_2)$$
and/or $$R_1\text{-His-Ile-Met-Asp-Trp-Trp-}R_2. \quad (R1\text{-SEQ ID NO: 9-}R_2)$$

$R_1$ is preferably selected from H or $R_5$—CO—, wherein $R_5$ is selected from the group formed by substituted or unsubstituted $C_1$-$C_{24}$ alkyl radical, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_3$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl ring of 3 to 10 members, and substituted or unsubstituted heteroarylalkyl of 2 to 24 carbon atoms and 1 to 3 atoms other than carbon and an alkyl chain of 1 to 6 carbon atoms. Even more preferably, R is selected from H, acetyl (hereinafter, Ac), tert-butanoyl, hexanoyl, 2-methylhexanoyl, cyclohexanecarboxyl, octanoyl, decanoyl, lauroyl myristoyl, palmitoyl (hereinafter, Pal), stearoyl, oleoyl and linoleoyl. Even more preferably, $R_1$ is Ac.

Preferably, $R_2$ is $NH_2$.

Hence, more preferably, $R_1$ is Ac and $R_2$ is $NH_2$.

Therefore, in this preferred embodiment, preferably, the sequence of a peptide in accordance with the present invention is:

(Ac-SEQ ID NO: 5-$NH_2$)
Ac-His-Ile-Leu-Asp-Met-Trp-$NH_2$;

(Ac-SEQ ID NO: 6-$NH_2$)
Ac-His-Ile-Met-Asp-Phe-Trp-$NH_2$;

(Ac-SEQ ID NO: 7-$NH_2$)
Ac-His-Ile-Leu-Asp-Trp-Trp-$NH_2$;

(Ac-SEQ ID NO: 8-$NH_2$)
Ac-His-Ala-Leu-Arg-Phe-Trp-$NH_2$;
and/or (Ac-SEQ ID NO: 9-$NH_2$)
Ac-His-Ile-Met-Asp-Trp-Trp-$NH_2$.

In another preferred embodiment, the sequence of a peptide of the present invention is in accordance with formula (II):

$$R_1\text{-}AA_1\text{-}AA_2\text{-}AA_3\text{-}AA_4\text{-}R_2 \tag{II}$$

their cosmetically and pharmaceutically acceptable isomers, salts, solvates and/or derivatives and mixtures thereof, wherein:
$AA_1$ is selected from the group of amino acids with positively charged side-chain;
$AA_2$ is any amino acid;
$AA_3$ is selected from the group of amino acids with positively charged side-chain;
$AA_4$ is selected from the group of amino acids with aromatic side-chain; $R_1$ is selected from H, substituted or unsubstituted non-cyclic aliphatic, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO— wherein $R_5$ is selected from the group formed by substituted or unsubstituted $C_1$-$C_{24}$ alkyl radical, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_3$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl ring of 3 to 10 members, and substituted or unsubstituted heteroarylalkyl of 2 to 24 carbon atoms and 1 to 3 atoms other than carbon and an alkyl chain of 1 to 6 carbon atoms; and
$R_2$ is selected from H, —$NR_3R_4$—, —$OR_3$ and —$SR_3$, wherein $R_3$ and $R_4$ are independently selected from H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl.

More preferably, in this preferred embodiment, in formula (II):
$AA_1$ is selected from the group of Lys, Arg and His;
$AA_2$ is any amino acid;
$AA_3$ is selected from the group of Lys, Arg and His; and
$AA_4$ is selected from the group of Phe, Tyr and Trp.

More preferably, in this preferred embodiment, in formula (II):
$AA_1$ is selected from the group of Arg;
$AA_2$ is any amino acid;
$AA_3$ is selected from the group of Arg; and
$AA_4$ is selected from the group of Phe.

Even more preferably, in this preferred embodiment, the sequence of a peptide in accordance with the present invention is:

($R_1$-SEQ ID NO: 10-$R_2$)
$R_1$-Arg-Arg-Arg-Phe-$R_2$;
and/or ($R_1$-SEQ ID NO: 11-$R_2$)
$R_1$-Arg-Met-Arg-Phe-$R_2$.

$R_1$ is preferably selected from H or $R_5$—CO—, wherein $R_5$ is selected from the group formed by substituted or unsubstituted $C_1$-$C_{24}$ alkyl radical, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_3$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl ring of 3 to 10 members, and substituted or unsubstituted heteroarylalkyl of 2 to 24 carbon atoms and 1 to 3 atoms other than carbon and an alkyl chain of 1 to 6 carbon atoms. Even more preferably, $R_1$ is selected from H, acetyl Ac, tert-butanoyl, hexanoyl, 2-methylhexanoyl, cyclohexanecarboxyl, octanoyl, decanoyl, lauroyl myristoyl, Pal, stearoyl, oleoyl and linoleoyl. Even more preferably, $R_1$ is Ac.

Preferably, $R_2$ is $NH_2$.

Hence, more preferably, $R_1$ is Ac and $R_2$ is $NH_2$.

Therefore, in this preferred embodiment, the sequence of a peptide in accordance with the present invention is:

(Ac-SEQ ID NO: 10-$NH_2$)
Ac-Arg-Arg-Arg-Phe-$NH_2$;
and/or (Ac-SEQ ID NO: 11-$NH_2$)
Ac-Arg-Met-Arg-Phe-$NH_2$.

The peptides of the present invention may be synthesized and produced by any means known in the state of the art. For example, they may be synthesized and produced by chemical synthesis (preferably, by means of solid phase peptide synthesis), expressing said peptides in cell cultures or by means of transgenic production of the peptide in plants or animals. In addition, the peptides of the present invention may be purified by any means known in the state of the art.

As it is apparent from the examples included below, the peptides of the present invention provide for an effective interference of the interaction between Munc18 and Syntaxin-1, leading, at a presynaptic level, to an inhibition of acetylcholine release and, hence, an inhibition of muscular contraction. Also, as can be derived from the examples included below, the peptides of the present invention have a direct effect at a postsynaptic level by inducing muscle relaxation directly in muscle cells. Therefore, the peptides of the present invention solve the above-mentioned problems and provide for additional or alternative peptides able to treat (prevent, reduce and/or eliminate) aesthetical signs and/or diseases related with dysregulation of neuronal exocytosis and/or muscle contractility.

In a second aspect, the present invention refers to a composition comprising at least one peptide in accordance with the present invention.

It is contemplated that the composition of the present invention comprises one type of peptide of the present invention or a combination or mixture of different peptides of the present invention.

In a preferred embodiment, the composition of the present invention is a cosmetic composition.

The cosmetic composition of the present invention comprises a cosmetically effective amount of the at least one peptide of the present invention. More preferably, the cosmetic composition of the present invention comprises from 0.0001% to 0.05% (m/v) of at least one peptide of the present invention, more preferably, from 0.0005% to 0.005% (m/v) of at least one peptide of the present invention and, even more preferably from 0.05%-0.001% (m/v) of at least one peptide of the present.

The cosmetic composition of the present invention, as a consequence of the activity of the peptides of the present invention (this is, inhibition of the interaction between Munc18 and Syntaxin-1 and, hence, inhibition of the release of neurotransmitters and modulation muscular contraction), provides for the prevention, reduction and/or elimination of skin aging and/or expression signs (preferably, wrinkles). More precisely, the cosmetic composition of the present invention provides for the prevention, reduction and/or elimination of facial expression wrinkles, more preferably, wrinkles in the forehead, wrinkles in the space between the eyebrows and/or wrinkles and fine lines around the mouth and/or around the eyes.

It is contemplated that the cosmetic composition of the present invention also comprises at least one additional cosmetic ingredient. Said additional cosmetic ingredient can be at least one excipient and/or at least one additional cosmetic active ingredient.

The additional cosmetic ingredients comprise those usually used in the state of the art as, for example, adjuvants such as stabilizer, solubilizer, vitamin, colorant and perfumery; carriers; and/or other cosmetic active ingredients.

Said additional cosmetic ingredients, must be physically and chemically compatible with the rest of the components of the composition and, especially, with the peptides of the present invention comprised in the composition of the present invention. Likewise, the nature of said additional cosmetic ingredients must not unacceptably alter the benefits of the peptides and compositions of the present invention. Said additional cosmetic ingredients may be of a synthetic or natural origin, such as, for example, plant extracts, or they can be derived from a biofermentation process (see, for example, CTFA Cosmetic Ingredient Handbook, Eleventh Edition (2006)).

It is contemplated that the additional cosmetic ingredients mentioned above comprise those ingredients commonly used in compositions for caring for; cleaning skin and/or hair; and/or deodorants and/or creams to prevent hyperhidrosis; such as, for example, agents inhibiting melanin synthesis, whitening or depigmenting agents, anti-aging agents, agents inhibiting NO-synthase, antioxidants, anti-atmospheric pollution and/or free radical trapping agents, anti-glycation agents, emulsifying agents, emollients, organic solvents, liquid propellants, skin conditioners such as for example wetting agents, moisture retaining substances, alpha hydroxy acids, moisturizers, vitamins, pigments or colorants, dyes, gelling polymers, thickeners, surfactants, softeners, other anti-wrinkle agents, agents capable of reducing or eliminating bags under the eyes, exfoliating agents, antimicrobial agents, antifungal agents, bactericides, agents stimulating dermal or epidermal macromolecule synthesis and/or capable of preventing or inhibiting their degradation, such as for example agents stimulating collagens synthesis, agents stimulating elastin synthesis, agents stimulating laminin synthesis, agents inhibiting collagen degradation, agents inhibiting elastin degradation, agents stimulating fibroblast proliferation, agents stimulating keratinocyte proliferation, agents stimulating keratinocyte differentiation, agents stimulating lipid synthesis and synthesis of components of the stratum corneum (ceramides, fatty acids, etc.), dermorelaxing agents, agents stimulating glycosaminoglycan synthesis, DNA repairing agents, DNA protecting agents, agents stimulating proteosome activity, anti-pruritus agents, agents for treating sensitive skin, reaffirming agents, astringent agents, sebum production regulating agents, agents stimulating lipolysis, anti-cellulite agents, calming agents, anti-inflammatory agents, agents acting on capillary circulation and/or microcirculation, agents acting on cell mitochondria, agents intended to improve the dermo-epidermal junction, preservatives, perfumes, chelating agents, plant extracts, essential oils, marine extracts, agents derived from a biofermentation process, mineral salts, cell extracts and/or solar filters (organic or mineral photoprotective agents active against ultraviolet A and B rays) among others.

In an embodiment, at least one of the additional cosmetic ingredients is a cosmetic active principle or substance which may exert the same, similar, complementary or different cosmetic activities as those disclosed above for the peptides of the present invention. It is contemplated that the cosmetic composition of the present invention comprises other anti-wrinkling or anti-aging agents, for example, collagen, elastin, growth factors, hyaluronic acid boosters, barrier function agents, illuminating agents, agents stimulating the expression and/or synthesis of collagen I, III, IV and/or VI and laminin; agents stimulating the synthesis of glycosaminoglycans or hyaluronic acid; agents stimulating the expression and/or synthesis of elastin and other elastic fibers-related proteins; agents inhibiting collagen and/or elastic fibers degradation; agents stimulating the expression and/or synthesis of mitochondria-related proteins (for example, sirtuins and aconitase); agents stimulating the expression and/or synthesis of focal adhesion proteins; agents stimulating keratinocytes and/or fibroblasts proliferation and/or differentiation; antioxidants; anti-atmospheric pollution and/or free radical trapping agents; anti-glycation agents; detoxifying agents; agents decreasing chronological aging, environmental aging and inflammation aging; and agents decreasing melanin production and/or inhibiting tyrosinase and/or agents stimulating lipid synthesis and synthesis of components of the epidermis (keratins) and more specifically the stratum corneum (keratins, ceramides, filaggrin, loricrin and SPRR1B). More preferably, the at least one of the additional cosmetic ingredients is Argireline® (Acetyl Hexapeptide-8), Leuphasyl® (Pentapeptide-3), Inyline® (Acetyl Hexapeptide-30), Syn-Ake® (Tripeptide-3) or combinations thereof.

In addition, the cosmetic composition of the present invention (or the peptide of the present invention) can be formulated in any form usually used in the state of the art as, for example, solution, suspension, emulsion, paste, gel, cream, powder, spray, lotion, oil, liniment, serum, mousse, ointment, bar or pencil including "leave on" and "rinse-off" formulations. The cosmetic composition of the present invention can also be incorporated by means of techniques known in the state of the art to different types of solid accessories such as towelettes, hydrogels, adhesive (or non-adhesive) patches or face masks, or it could be incorporated to different make-up line products such as concealers, make-up foundations, lotions or make-up removal lotions, among others.

It is also contemplated that the cosmetic composition of the present invention or a peptide of the present invention, both as disclosed herein, can also be incorporated in cosmetic sustained release systems and/or carriers such as liposomes, milliparticles, microparticles and nanoparticles, as well as in sponges, vesicles, micelles, millispheres, microspheres, nanospheres, liposphere, millicapsules, microcapsules and nanocapsules, as well as in microemulsions and nanoemulsions, for the purpose of obtaining greater penetration of the active ingredient.

In a preferred embodiment, the cosmetic composition of the present invention is suited or adapted to be applied by means of iontophoresis, more preferably, in the face and/or the body of a subject, more preferably, in the face, neck, hands and/or armpits of a subject, even more preferably in the face and/or neck of a subject (preferably, a human).

In another preferred embodiment, the cosmetic composition of the present invention is suited or adapted to be applied by means of subcutaneous injection, more preferably, in the face and/or the body of a subject, more preferably, in the face, neck, hands and/or armpits of a subject, even more preferably in the face and/or neck of a subject (preferably, a human).

In the most preferred embodiment, the cosmetic composition of the present invention is suited or adapted to be applied topically (more prefereably, in the form of a cream), more preferably, in the face and/or the body of a subject, more preferably, in the face, neck, hands and/or armpits of a subject, even more preferably in the face and/or neck of a subject (preferably, a human).

In another preferred embodiment, the composition of the present invention is a pharmaceutical composition.

It is contemplated that the composition of the present invention comprises one type of peptide of the present invention or a combination or mixture of different peptides of the present invention.

The pharmaceutical composition of the present invention comprises a pharmaceutically effective amount of the at least one peptide of the present invention.

The pharmaceutical composition of the present invention, as a consequence of the activity of the peptides of the present invention (this is, inhibition of the release of neurotransmitters and, modulation of muscular contraction), provides for the prevention and/or treatment of diseases associated with neuronal exocytosis and/or muscle contractility disorder, more precisely for the prevention and/or treatment of diseases associated with a dysregulation of SNARE complex formation, dysregulation of striated muscle contraction, dysregulation of acetylcholine and/or CGRP release and/or dysregulation of $Ca^{2+}$ channel activation, preferably, senile dementia, Alzheimer's-related dementia, AIDS-related dementia, epilepsy, amiotrophic sclerosis, multiple/lateral sclerosis, chronic migraine, mastocytosis, dystonia or anxiety disorders.

The pharmaceutical composition of the present invention also provides for the treatment of myotonia, myotonic dystrophy, myotonia congenita, Parkinson disease, Secondary Parkinsonism, Huntington disease, spasticity, Tardive Dysinesia (TD) or dystonia (blepharospasm, Meige syndrome, hand cramps, limb dystonia or strabismus).

The pharmaceutical composition can be in any form known in the state of the art which is suited for the chosen route. It is contemplated that the pharmaceutical composition of the present invention is suited or adapted to be administered by any means and any route known in the state of the art (for example, subcutaneously, intramuscularly, intravenously or orally; in the latter case, for example, in the form of a saline solution and/or of a biodegradable material, such as polymers of polylactic acid (PLA), polyglycolic acid (PGA) polylactic acid-glycolic acid copolymers, polycaprolactones and/or cholesterol).

It is contemplated that the pharmaceutical composition of the present invention also comprises at least one additional pharmaceutical ingredient. Said additional pharmaceutical ingredient can be at least one excipient and/or at least one additional pharmaceutical active ingredient. It is contemplated that the at least one additional pharmaceutical active ingredient is a Benzodiazepine, Clonazepam, Lorazepam, Diazepam, Baclofen, an Anticholinergic, Trihexyphenidyl, Benztropine, a Dopamine-depleting agent, Tetrabenazine, Clozapine or combinations thereof.

In a third aspect, as stated above, the present invention refers to a peptide or a composition in accordance with the present invention (this is, in accordance with what has been stated above) for use in medicine.

As noted above and as it is directly derivable from the examples included below, the peptides of the present invention (and, hence, the compositions comprising them), are able to inhibit the release of acetylcholine and muscular contraction and, therefore, due to said activities they are useful as medicaments.

In a preferred embodiment, the peptides or compositions of the present invention are for use in the prevention and/or treatment (preferably, treatment) of a neuronal exocytosis and/or muscle contractility disorder.

The muscle contractility disorder is, preferably, muscle hypercontractility.

Preferably, the neuronal exocytosis and/or muscle contractility disorder is a disease associated with a dysregulation of SNARE complex formation, striated muscle contraction, acetylcholine and/or CGRP release, and/or $Ca^{2+}$ channel activation.

More preferably, the neuronal exocytosis and/or muscle contractility disorder is selected from senile dementia, Alzheimer's-related dementia, AIDS-related dementia, epilepsy, amiotrophic sclerosis, multiple/lateral sclerosis, mastocytosis, chronic migraine, dystonia or anxiety disorders.

Therefore, in a preferred embodiment, the peptides or compositions of the present invention are for use in the prevention and/or treatment of senile dementia, Alzheimer's-related dementia, AIDS-related dementia, epilepsy, amiotrophic sclerosis, multiple/lateral sclerosis, mastocytosis, chronic migraine, dystonia or anxiety disorders. Regarding said diseases, senile dementia, Alzheimer's-related dementia, AIDS-related dementia, epilepsy, amiotrophic sclerosis, multiple/lateral sclerosis, chronic migraine and anxiety disorders are neuronal exocytosis disorders. On the other side, dystonia is a muscle contractility disorder.

Preferably, the dystonia is selected from blepharospasm, Meige syndrome, hand cramps, limb dystonia or strabismus.

In another preferred embodiment, the peptides or compositions of the present invention are for use in the prevention and/or treatment of myotonia, myotonic dystrophy, myotonia congenita, Parkinson disease, Secondary Parkinsonism, Huntington disease, spasticity or Tardive Dysinesia (TD). Said diseases are muscle contractility disorders.

Preferably, the peptide or composition of the present invention is used in a therapeutically effective amount.

In a preferred embodiment, the peptides and compositions of the present invention are for use in a mammal, more preferably in a human.

In a preferred embodiment, the composition is a pharmaceutical composition in accordance with what has been stated above.

The peptide or composition of the present invention can be used by any means or through any route known in the state of the art. In any case, the peptide or composition will be adapted to the chosen means and/or route (for example, subcutaneously, intramuscularly, intravenously or orally; in the latter case, for example, in the form of a saline solution and/or of a biodegradable material, such as polymers of polylactic acid (PLA), polyglycolic acid (PGA) polylactic acid-glycolic acid copolymers, polycaprolactones and/or cholesterol).

In a fourth aspect, the present invention refers to a method for the prevention and/or treatment (preferably, treatment) of neuronal exocytosis and/or muscle contractility disorders, comprising administering a peptide or a composition of the present invention to a subject in need thereof.

The muscle contractility disorder is, preferably, muscle hypercontractility.

Preferably, the neuronal exocytosis and/or muscle contractility disorder is a disease associated with a dysregulation of SNARE complex formation, dysregulation of striated muscle contraction, dysregulation of acetylcholine and/or CGRP release and/or dysregulation of $Ca^{2+}$ channel activation.

More preferably, the neuronal exocytosis and/or muscle contractility disorder is selected from senile dementia, Alzheimer's-related dementia, AIDS-related dementia, epilepsy, amiotrophic sclerosis, multiple/lateral sclerosis, mastocytosis, chronic migraine, dystonia or anxiety disorders.

Regarding said diseases, senile dementia, Alzheimer's-related dementia, AIDS-related dementia, epilepsy, amiotrophic sclerosis, multiple/lateral sclerosis, chronic migraine and anxiety disorders are neuronal exocytosis disorders. On the other side, dystonia is a muscle contractility disorder.

Preferably, the dystonia is selected from blepharospasm, Meige syndrome, hand cramps, limb dystonia or strabismus.

In another preferred embodiment, the neuronal exocytosis and/or muscle contractility disorder is a muscle contractility disorder selected from myotonia, myotonic dystrophy, myotonia congenita, Parkinson disease, Secondary Parkinsonism, Huntington disease, spasticity or Tardive Dysinesia (TD).

Preferably, the peptide or composition of the present invention is used in a therapeutically effective amount.

In a preferred embodiment, the subject in need of the method of treatment of the present invention is a mammal, more preferably, a human.

In a preferred embodiment, the composition is a pharmaceutical composition in accordance with what has been stated above.

The peptide or composition of the present invention can be used by any means or through any route known in the state of the art. In any case, the peptide or composition will be adapted to the chosen means and/or route (for example, subcutaneously, intramuscularly, intravenously or orally; in the latter case, for example, in the form of a saline solution and/or of a biodegradable material, such as polymers of polylactic acid (PLA), polyglycolic acid (PGA) polylactic acid-glycolic acid copolymers, polycaprolactones and/or cholesterol).

As already stated above, in a fifth aspect, the present invention refers to the use as a cosmetic of the peptide or cosmetic composition of the present invention to prevent, reduce and/or eliminate signs related with dysregulation of neuronal exocytosis and/or of muscle contractility in a subject.

As it is evident, the signs mentioned above are cosmetic signs.

Dysregulation of muscle contractility is, preferably muscle hypercontractility.

Preferably, the cosmetic signs related with dysregulation of neuronal exocytosis and/or muscle hypercontractility are skin aging and/or expression signs.

The cosmetic signs of skin aging are, preferably, wrinkles.

In the most preferred embodiment, the skin aging and/or expression signs are facial wrinkles (preferably, expression signs) and/or facial asymmetry.

In a preferred embodiment, the peptide or the cosmetic composition of the present invention is applied by means of iontophoresis, more preferably, in the face and/or the body of the subject, more preferably, in the face, neck, hands and/or armpits of the subject, even more preferably in the face and/or neck of the subject (preferably, a human).

In another preferred embodiment, the peptide or the cosmetic composition of the present invention is applied by means of subcutaneous injection, more preferably, in the face and/or the body of the subject, more preferably, in the face, neck, hands and/or armpits of the subject, even more preferably in the face and/or neck of the subject (preferably, a human).

In the most preferred embodiment, the peptide or the cosmetic composition of the present invention is applied topically (more preferably in the form of a cream), more preferably, in the face and/or the body of the subject, more preferably, in the face, neck, hands and/or armpits of the subject, even more preferably in the face and/or neck of the subject (preferably, a human).

Preferably, the subject is a mammal, even more preferably, a human.

In addition, in the use as a cosmetic of the present invention, the peptide or the cosmetic composition of the present invention are used in a cosmetically effective amount. More preferably, the peptide of the present invention is used at a concentration of 0.0001% to 0.05% (m/v), more preferably, from 0.0005% to 0.005% (m/v) and, even more preferably from 0.05%-0.001% (m/v).

It is contemplated that the cosmetic composition of the present invention, as already stated above, also comprises at least one additional cosmetic ingredient. Said additional cosmetic ingredient can be at least one excipient and/or at least one additional cosmetic active ingredient, which can be as explained above. It is also contemplated that the peptide of the present invention is used in combination with at least one additional cosmetic ingredient which is in accordance with what has been stated above.

In addition, the peptide of the present invention and the cosmetic composition of the present invention can be formulated in any form usually used in the state of the art as, for example, solution, suspension, emulsion, paste, gel, cream, powder, spray, lotion, oil, liniment, serum, mousse, ointment, bar or pencil including "leave on" and "rinse-off" formulations. The peptide and the cosmetic composition of the present invention can also be incorporated by means of techniques known in the state of the art to different types of solid accessories such as towelettes, hydrogels, adhesive (or non-adhesive) patches or face masks, or it could be incorporated to different make-up line products such as concealers, make-up foundations, lotions or make-up removal lotions, among others.

It is also contemplated that the cosmetic composition of the present invention or a peptide of the present invention, both as disclosed herein, can also be incorporated in cosmetic sustained release systems and/or carriers such as liposomes, milliparticles, microparticles and nanoparticles, as well as in sponges, vesicles, micelles, millispheres, microspheres, nanospheres, liposphere, millicapsules, microcapsules and nanocapsules, as well as in microemulsions and nanoemulsions, for the purpose of obtaining greater penetration of the active ingredient.

In a sixth aspect, the present invention refers to the cosmetic use of a peptide or a cosmetic composition of the present invention (this is, as explained above) to prevent, reduce and/or eliminate signs related with dysregulation of neuronal exocytosis and/or of muscle contractility in a subject.

As it is evident, the signs mentioned above are cosmetic signs.

Dysregulation of muscle contractility is, preferably muscle hypercontractility

Preferably, the cosmetic signs related with dysregulation of neuronal exocytosis and/or muscle hypercontractility are skin aging and/or expression signs.

The cosmetic signs of skin aging are, preferably, wrinkles.

In the most preferred embodiment, the skin aging and/or expression signs are expression facial wrinkles (preferably, expression wrinkles) and/or facial asymmetry.

In a preferred embodiment, the peptide or the cosmetic composition of the present invention is applied by means of iontophoresis, more preferably, in the face and/or the body of the subject, more preferably, in the face, neck, hands and/or armpits of the subject, even more preferably in the face and/or neck of the subject.

In another preferred embodiment, the peptide or the cosmetic composition of the present invention is applied by means of subcutaneous injection, more preferably, in the face and/or the body of the subject, more preferably, in the face, neck, hands and/or armpits of the subject, even more preferably in the face and/or neck of the subject.

In the most embodiment, the peptide or the cosmetic composition of the present invention is applied topically (more preferably in the form of a cream), more preferably, in the face and/or the body of the subject, more preferably, in the face, neck, hands and/or armpits of the subject, even more preferably in the face and/or neck of the subject (preferably, a human).

Preferably, the subject is a mammal, even more preferably a human.

In addition, in the cosmetic use of the present invention, the peptide or the cosmetic composition of the present invention are used in a cosmetically effective amount. More preferably, the peptide of the present invention is used at a concentration of 0.0001% to 0.05% (m/v), more preferably, from 0.0005% to 0.005% (m/v) and, even more preferably from 0.05%-0.001% (m/v).

It is contemplated that the cosmetic composition of the present invention, as already stated above, also comprises at least one additional cosmetic ingredient. Said additional cosmetic ingredient can be at least one excipient and/or at least one additional cosmetic active ingredient, which can be as explained above. It is also contemplated that the peptide of the present invention is used in combination with at least one additional cosmetic ingredient which is in accordance with what has been stated above.

In addition, the peptide of the present invention and the cosmetic composition of the present invention can be formulated in any form usually used in the state of the art as, for example, solution, suspension, emulsion, paste, gel, cream, powder, spray, lotion, oil, liniment, serum, mousse, ointment, bar or pencil including "leave on" and "rinse-off" formulations. The peptide and the cosmetic composition of the present invention can also be incorporated by means of techniques known in the state of the art to different types of solid accessories such as towelettes, hydrogels, adhesive (or non-adhesive) patches or face masks, or it could be incorporated to different make-up line products such as concealers, make-up foundations, lotions or make-up removal lotions, among others.

It is also contemplated that the cosmetic composition of the present invention or a peptide of the present invention, both as disclosed herein, can also be incorporated in cosmetic sustained release systems and/or carriers such as liposomes, milliparticles, microparticles and nanoparticles, as well as in sponges, vesicles, micelles, millispheres, microspheres, nanospheres, liposphere, millicapsules, microcapsules and nanocapsules, as well as in microemulsions and nanoemulsions, for the purpose of obtaining greater penetration of the active ingredient.

As stated above, in a seventh aspect, the present invention refers to a method to prevent and/or reduce signs related with dysregulation of neuronal exocytosis and/or of muscle contractility in a subject in need thereof, characterized in that it comprises the use of a peptide or a cosmetic composition in accordance with the present invention.

The signs mentioned above are cosmetic signs.

Dysregulation of muscle contractility is, preferably muscle hypercontractility

Preferably, the cosmetic signs related with dysregulation of neuronal exocytosis and/or muscle hypercontractility are skin aging and/or expression signs.

Preferably, the cosmetic signs of skin aging are wrinkles.

In the most preferred embodiment, the skin aging and/or expression signs are facial wrinkles (preferably, expression wrinkles) and/or facial asymmetry.

In a preferred embodiment, the peptide or the cosmetic composition of the present invention is applied by means of iontophoresis, more preferably, in the face and/or the body of the subject, more preferably, in the face, neck, hands and/or armpits of the subject, even more preferably in the face and/or neck of the subject (preferably, a human).

In another preferred embodiment, the peptide or the cosmetic composition of the present invention is applied by means of subcutaneous injection, more preferably, in the face and/or the body of the subject, more preferably, in the face, neck, hands and/or armpits of the subject, even more preferably in the face and/or neck of the subject (preferably, a human).

In the most preferred embodiment, the peptide or the cosmetic composition of the present invention is applied topically (more preferably in the form of a cream), more preferably, in the face and/or the body of the subject, more preferably, in the face, neck, hands and/or armpits of the subject, even more preferably in the face and/or neck of the subject (preferably, a human).

Preferably, the subject is a mammal, even more preferably a human.

In addition, in the method of the present invention, the peptide or the cosmetic composition of the present invention are used in a cosmetically effective amount. More preferably, the peptide of the present invention is used at a concentration of 0.0001% to 0.05% (m/v), more preferably, from 0.0005% to 0.005% (m/v) and, even more preferably from 0.05%-0.001% (m/v).

It is contemplated that the cosmetic composition of the present invention, as already stated above, also comprises at least one additional cosmetic ingredient. Said additional cosmetic ingredient can be at least one excipient and/or at least one additional cosmetic active ingredient, which can be as explained above. It is also contemplated that the peptide of the present invention is used in combination with at least one additional cosmetic ingredient which is in accordance with what has been stated above.

In addition, the peptide of the present invention and the cosmetic composition of the present invention can be formulated in any form usually used in the state of the art as, for example, solution, suspension, emulsion, paste, gel, cream, powder, spray, lotion, oil, liniment, serum, mousse, ointment, bar or pencil including "leave on" and "rinse-off" formulations. The peptide and the cosmetic composition of the present invention can also be incorporated by means of techniques known in the state of the art to different types of solid accessories such as towelettes, hydrogels, adhesive (or non-adhesive) patches or face masks, or it could be incorporated to different make-up line products such as concealers, make-up foundations, lotions or make-up removal lotions, among others.

It is also contemplated that the cosmetic composition of the present invention or a peptide of the present invention, both as disclosed herein, can also be incorporated in cosmetic sustained release systems and/or carriers such as liposomes, milliparticles, microparticles and nanoparticles, as well as in sponges, vesicles, micelles, millispheres, microspheres, nanospheres, liposheres, millicapsules, microcapsules and nanocapsules, as well as in microemulsions and nanoemulsions, for the purpose of obtaining greater penetration of the active ingredient.

To allow a better understanding, the present invention is described in more detail below with reference to the enclosed drawings, which are presented by way of example, and with reference to illustrative and non-limitative examples.

FIG. 1 shows the percentage acetylcholine release in vitro by LAN cells treated with the analyzed peptides in comparison with the positive control (this is, establishing the percentage of acetylcholine release of the positive control sample as 100% and then performing the comparison with the rest of the samples). FIG. 1 shows the results obtained for peptides: Ac-SEQ ID NO: 5-$NH_2$ (A), Ac-SEQ ID NO: 6-$NH_2$ (B), Ac-SEQ ID NO: 7-$NH_2$ (C), Ac-SEQ ID NO: 8-$NH_2$ (D), Ac-SEQ ID NO: 9-$NH_2$ (E), Ac-SEQ ID NO: 10-$NH_2$ (F), Ac-SEQ ID NO: 11-$NH_2$ (G), Ac-SEQ ID NO: 13-$NH_2$ (H) and Ac-SEQ ID NO:14-$NH_2$ (I). All peptides, except Ac-SEQ ID NO: 8-$NH_2$ (D), were tested at concentrations of 0.001 mg/mL, 0.005 mg/mL and 0.01 mg/mL; and peptide Ac-SEQ ID NO: 8-$NH_2$ (D) was tested at 0.005 mg/mL and 0.05 mg/mL. For FIGS. 1(D) columns from left to right in the x-axis correspond to: basal state (cells without treatment), positive control (cells treated with 50 mM of KCl), cells treated with 100 nM of toxin (Botulinum neurotoxin A light chain (BoNT A LC) produced in accordance with Ibañez C., Blanes-Mira C., Fernández-Ballester G., Planells-Cases R., and Ferrer-Montiel A., (2004) Modulation of botulinum neurotoxin A catalytic domain stability by tyrosine phosphorylation, FEBS Letters 578, 121-127), cells treated with 0.1 µM Palmitoyl-Argireline® (palmitoyl-acetyl hexapeptide-8®) and cells treated with 0.005 mg/mL and 0.05 mg/mL of the corresponding peptide. On its side, for FIGS. 1(A) to 1(C) and 1(E) to 1(I), columns from left to right in the x-axis correspond to: basal state (cells without treatment), positive control (cells treated with 50 mM of KCl), cells treated with 100 nM of toxin (BoNT A LC) and cells treated with 0.001 mg/mL, 0.005 mg/mL and 0.01 mg/mL of the corresponding peptide. For FIGS. 1(A) to 1(I) the y axis shows the percentage of acetylcholine release (with regard to the positive control).

Figure 2A:
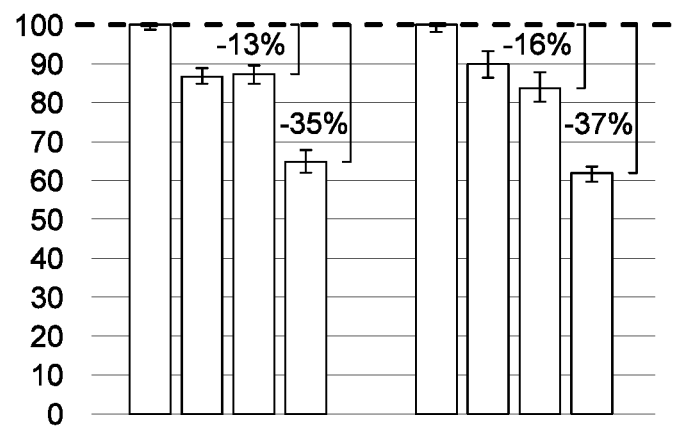
Figure 2B:
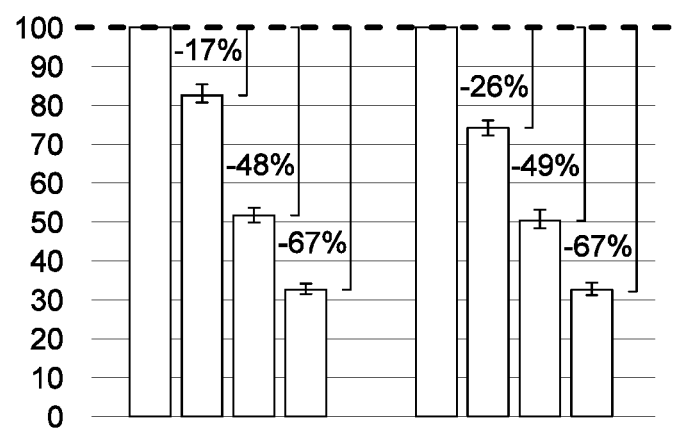
Figure 3A:
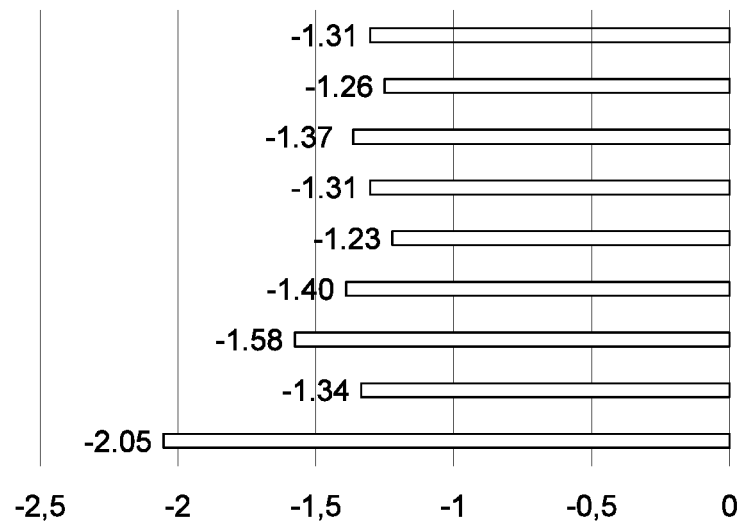
Figure 3B:
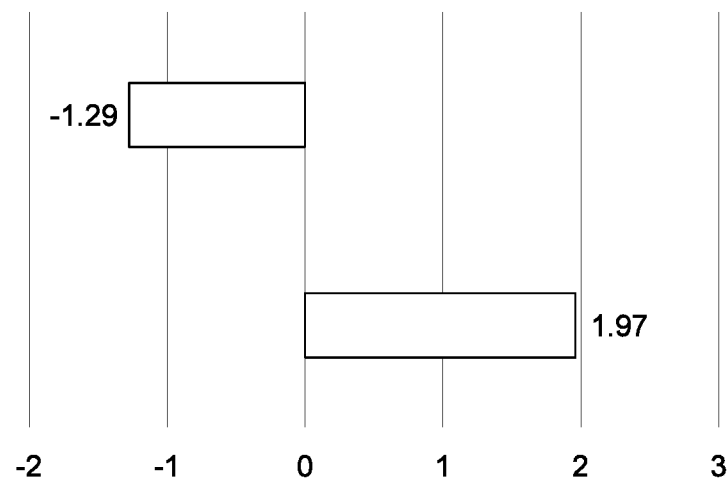
Figure 3C:
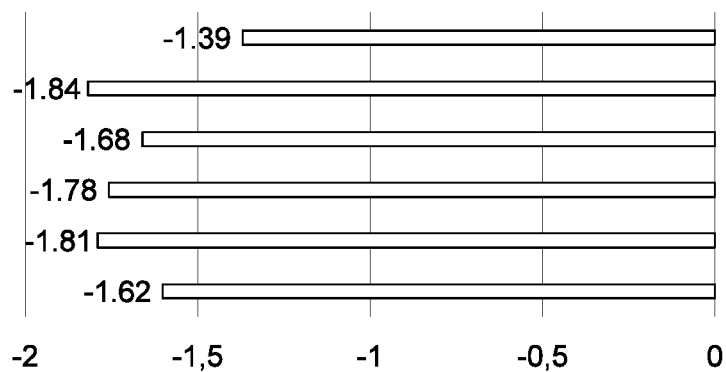
Figure 3D:
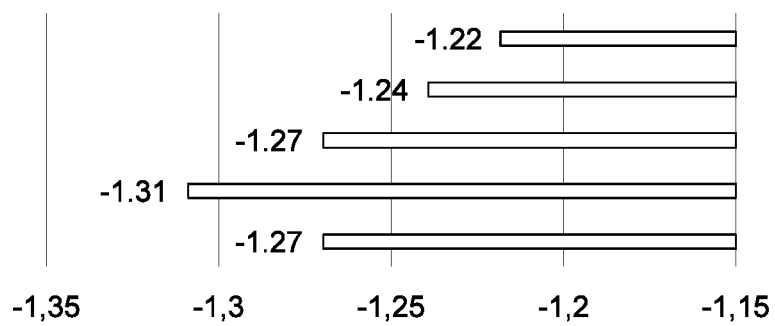

FIG. 2 shows the percentage of binding of the complex Munc18-Syntaxin-1 with respect to the control (no treatment), which represents 100% of binding. In FIG. 2 the capacity of peptides Ac-SEQ ID NO:8-$NH_2$ (A) and Ac-SEQ ID NO: 5-$NH_2$ (B) to inhibit the formation of the complex Munc18-Syntaxin-1 can be observed. Columns from left to right in the x-axis of both, FIGS. 2(A) and 2(B), correspond to: control and 0.1, 0.5 and 1 mM concentration of the corresponding peptide at a ratio Munc18 100 nM:Syntaxin-1 nM for the first group of columns (left group of columns) and, for the second group of columns, control and 0.1, 0.5 and 1 mM concentration of the corresponding peptide at a ratio Munc18 100 nM:Syntaxin-1 5 nM (right group of columns). For both figures the y axis shows the percentage of formation of the complex, being 100% the signal obtained without any treatment.

FIG. 3 shows the modulation in gene expression profile of human skeletal myocytes induced by the treatment with the peptides of the present invention. FIG. 3(A) shows the results obtained for the treatment with Ac-SEQ ID NO: 8-$NH_2$ (at a concentration of 0.05 and 0.5 mg/mL, during 6 hours), wherein bars, from top to bottom refer to the following genes: SCN3A (Sodium Voltage-Gated Channel Alpha Subunit 3), UTRN (Utrophin), ACTA1 (Actin alpha 1), TNNC1 (Troponin C1), CALM3 (Calmodulina 3), CAV1 (Caveolin 1), CACNB1 (Calcium Voltage-Gated Channel Auxiliary Subunit Beta 1), LRP4 (LDL Receptor Related Protein 4) and MYH1 (Myosin Heavy Chain 1). In FIG. 3(A) the results shown for genes MHY1, LRP4, CACNB1 and UTRN correspond to a treatment with 0.05 mg/mL, while the rest correspond to a 0.5 mg/mL treatment. FIG. 3(B) shows the results obtained for the treatment with Ac-SEQ ID NO: 8-$NH_2$ at a concentration of 0.5 mg/mL during 24 hours, wherein bars, from top to bottom refer to the following genes: RAPSN (Receptor Associated Protein of The Synapse) and ATP2A (ATPase Sarcoplasmic/Endoplasmic Reticulum $Ca^{2+}$ Transporting). FIG. 3(C) shows the results obtained for the treatment with Ac-SEQ ID NO: 5-$NH_2$ (at a concentration of 0.05 mg/mL and during 24 hours), wherein bars, from top to bottom refer to the following genes: UTRN (Utrophin), ACTA1 (Actin alpha 1), TNNC1 (Troponin C1), RAPSN (Receptor Associated Protein of The Synapse), SCN3A (Sodium Voltage-Gated Channel Alpha Subunit 3) and MYH1. FIG. 3(D) shows the results obtained for the treatment with Ac-SEQ ID NO: 10-$NH_2$ (at a concentration of 0.1 mg/mL and during 24 hours), wherein bars, from top to bottom refer to the following genes: UTRN (Utrophin), TNNC1 (Troponin C1), SCN3A (Sodium Voltage-Gated Channel Alpha Subunit 3), CHRNA1 (Cholinergic Receptor Nicotinic Alpha 1 Subunit) and CACNB1 (Calcium Voltage-Gated Channel Auxiliary Subunit Beta 1). In the four cases, x-axis refers to the fold change with regard to the basal state. A negative fold change refers to downregulation of gene expression while a positive fold change refers to upregulation.

Figure 4:
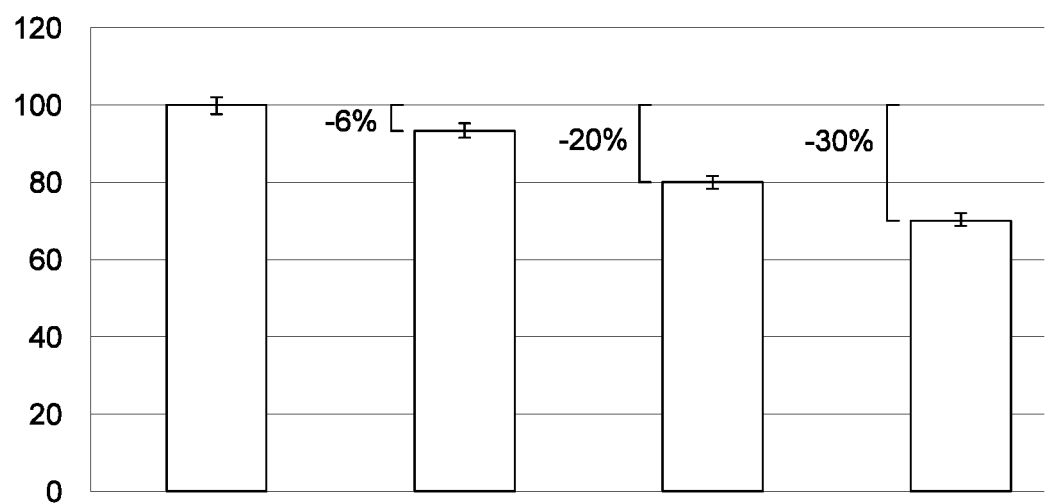

FIG. 4 shows the decrease in calcium influx on human skeletal muscle myocytes after treatment with peptide Ac-SEQ ID NO: 8-NH$_2$ and stimulation with 60 mM KCl with regard to the control (untreated sample stimulated with 60 mM KCl) which is established as 100%. Columns from left to right in the x-axis correspond to: control and 0.01, 0.05 and 0.1 mg/mL of peptide concentration. The y axis shows the percentage of decrease in calcium signal with regard to the control, established as 100% signal.

Figure 5A:
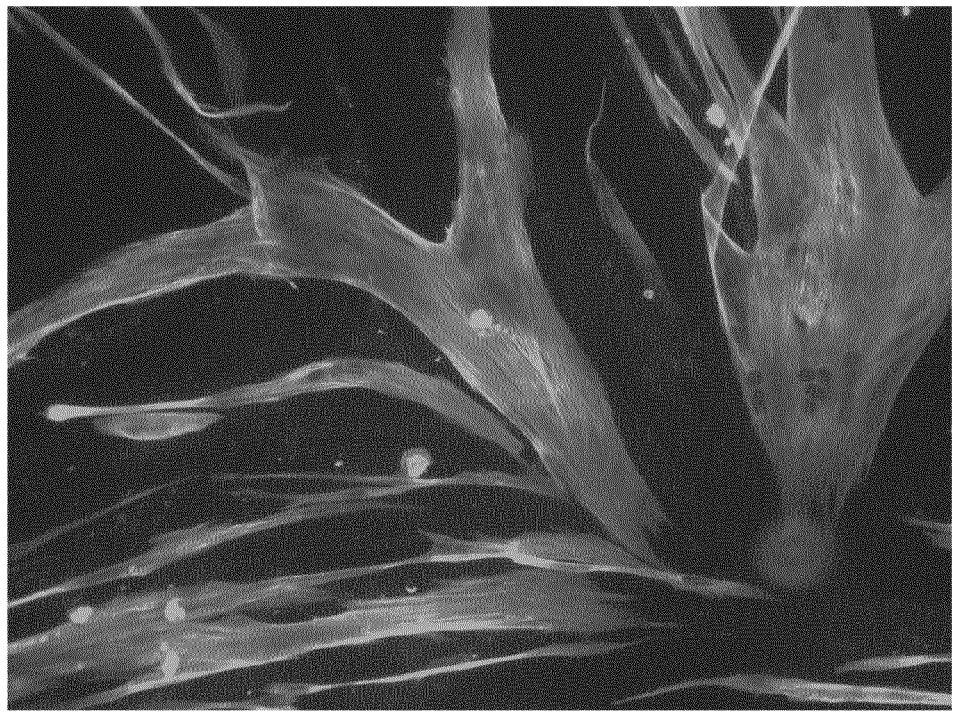
Figure 5B:
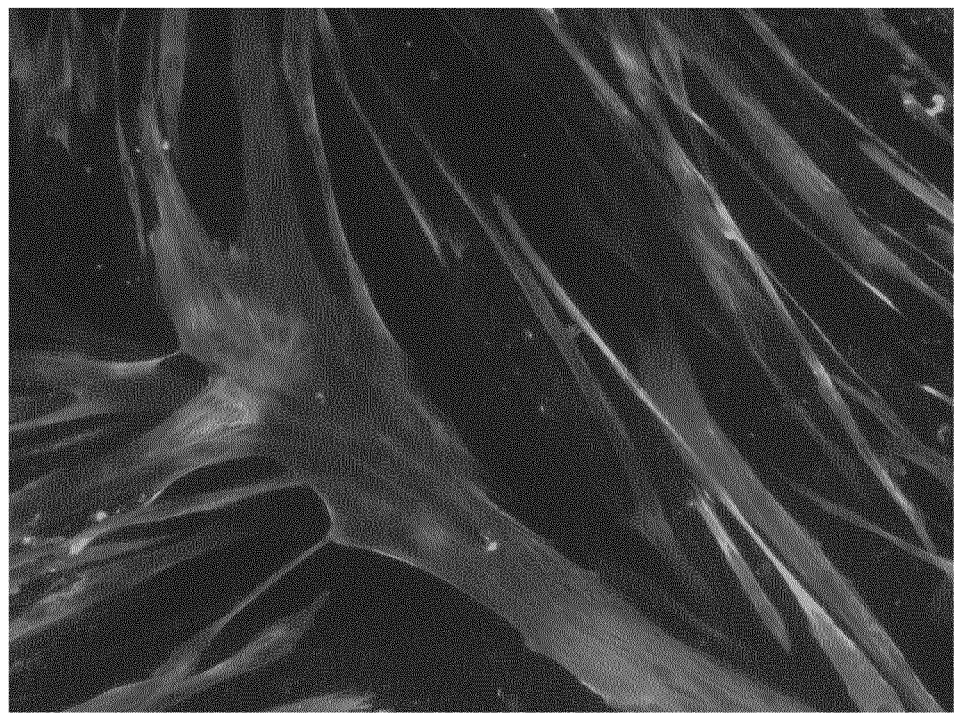

FIG. 5 shows representative images of the expression levels of myosin heavy chain protein, on non-treated primary human skeletal muscle cells (FIG. 5(A)) and on primary human skeletal muscle cells treated with 0.05 mg/mL of peptide Ac-SEQ ID NO: 8-NH$_2$ (FIG. 5(B)). A reduction of myosin heavy chain protein levels is observed in the primary human skeletal muscle cells treated with 0.05 mg/mL of peptide with regard to the non-treated cells, which can be seen as a loss of staining or signal in FIG. 5B in comparison with FIG. 5(A).

Figure 6:
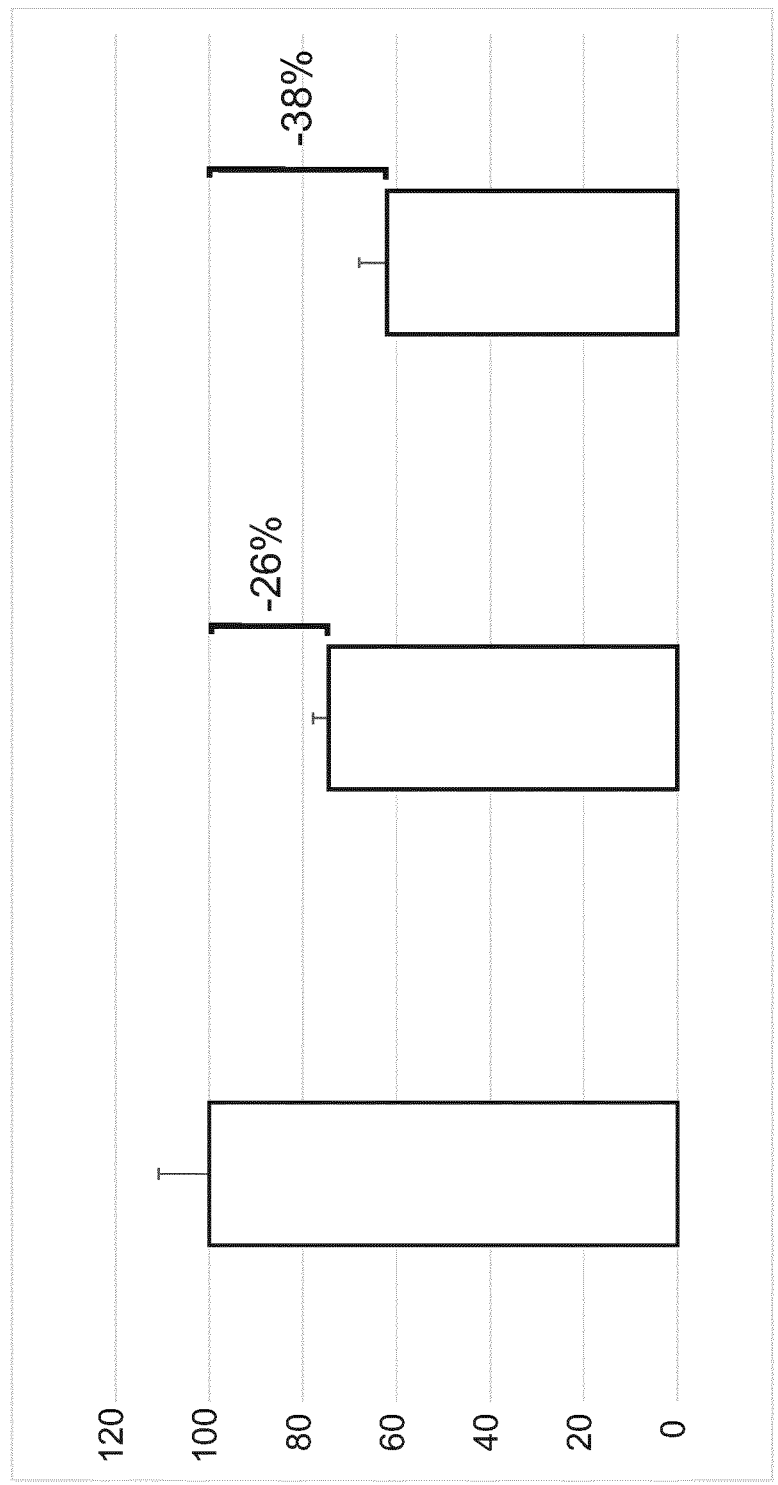

FIG. 6 shows the decrease of myosin heavy chain protein levels on primary human skeletal muscle cells after treatment with the peptide Ac-SEQ ID NO: 8-NH$_2$ with regard to the basal control (non-treated cells) which is established as 100%. Columns from left to right in the X-axis correspond to non-treated cells and 0.05 and 0.5 mg/ml of peptide concentration. The Y-axis shows the levels of myosin heavy chain protein with regard to the basal control, established as 100% signal (on the basis of the fluorescence signal observed for myosin heavy chain protein in each of the treatment groups, as measured by means of mean cell fluorescence).

Figure 7:
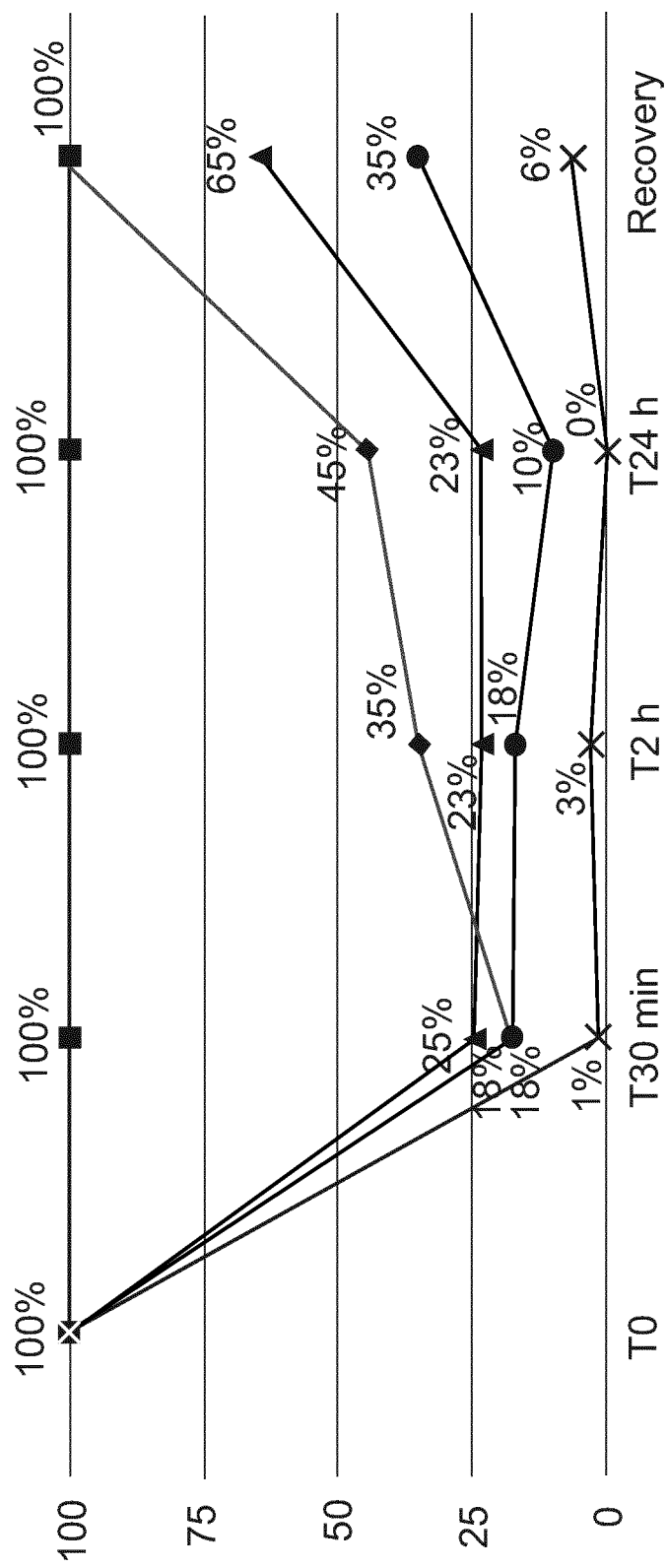

FIG. 7 shows the modulation in the contraction frequency observed on human motor neurons and human skeletal myocytes co-cultures after treatment with either peptide Ac-SEQ ID NO: 8-NH$_2$, acetyl hexapeptide-8, as a benchmark control, or α-bungarotoxin, as a positive control of inhibition, with regard to the basal control (non-treated cells) which is established as 100%. The line with squares represents the contraction frequency of the non-treated cells (basal control). The line with crosses represents the contraction frequency by the positive control of contraction inhibition, α-bungarotoxin. The line with diamonds represents the contraction frequency by the benchmark acetyl hexapeptide-8 at 0.5 mg/ml. The line with circles represents the contraction frequency by peptide Ac-SEQ ID NO: 8-NH$_2$ at 0.1 mg/ml; and the line with triangles represents the contraction frequency by peptide Ac-SEQ ID NO: 8-NH$_2$ at 0.05 mg/ml. The X-axis corresponds to the length of the treatment by the different actives and it points out different time points: TO, T30 min, T2 h, T24 h and recovery. TO corresponds to the contractions before the treatment with the above-mentioned compounds; T30 min corresponds to the 30 min-treatment; T2 h corresponds to the 2 h-treatment; T24 h corresponds to the 24 h-treatment and Recovery corresponds to the 24 h incubation after removal of all compounds. The Y-axis shows the percentage of contraction frequency with regard to the basal control (non-treated cells), established as 100% signal.

Figure 8:
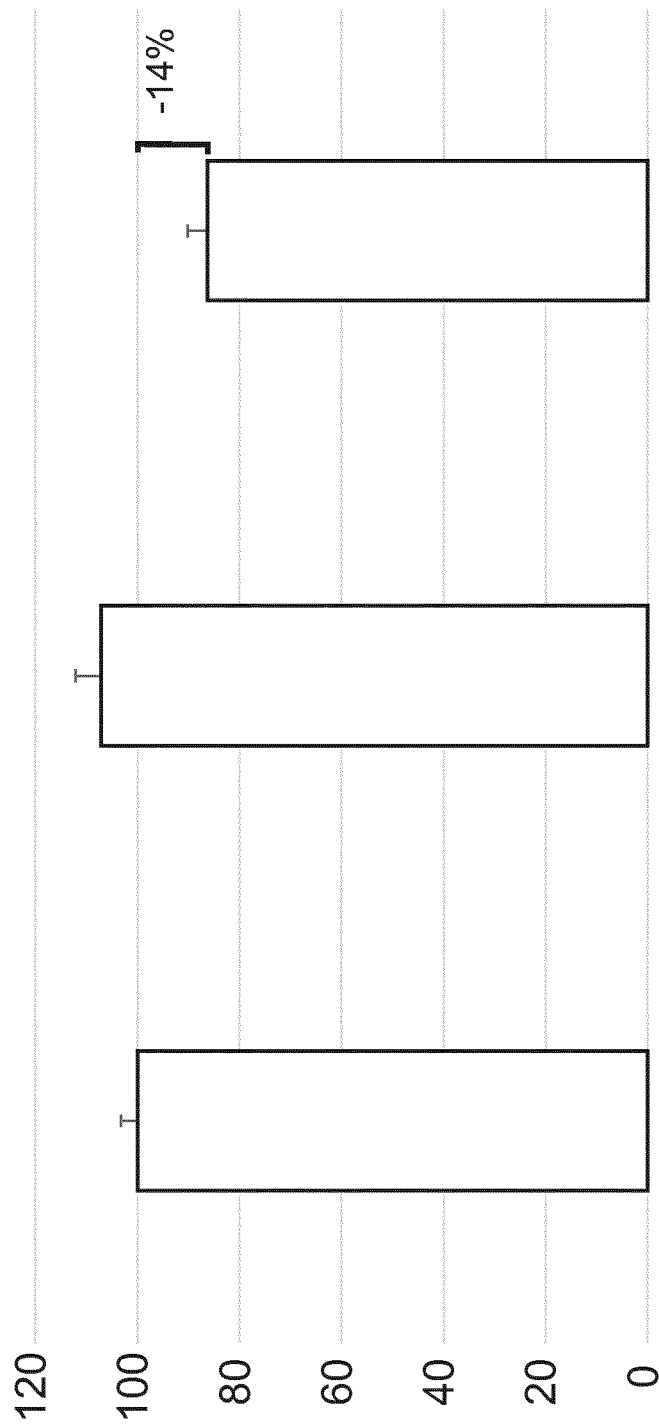

FIG. 8 shows the decrease of exocytosis on a human neuroblastoma cell line after treatment with the peptide Ac-SEQ ID NO: 8-NH$_2$ or the benchmark acetyl hexapeptide-8 with regard to the basal control of non-treated cells which is established as 100%. Columns from left to right in the X-axis correspond to non-treated cells, cells treated with 1 mg/ml of acetyl hexapeptide-8 and cells treated with 0.01 mg/ml of peptide Ac-SEQ ID NO: 8-NH$_2$. The Y-axis shows the percentage of the fluorescence signal corresponding to the level of exocytosis with regard to the basal control, established as 100% level.

Figure 9:
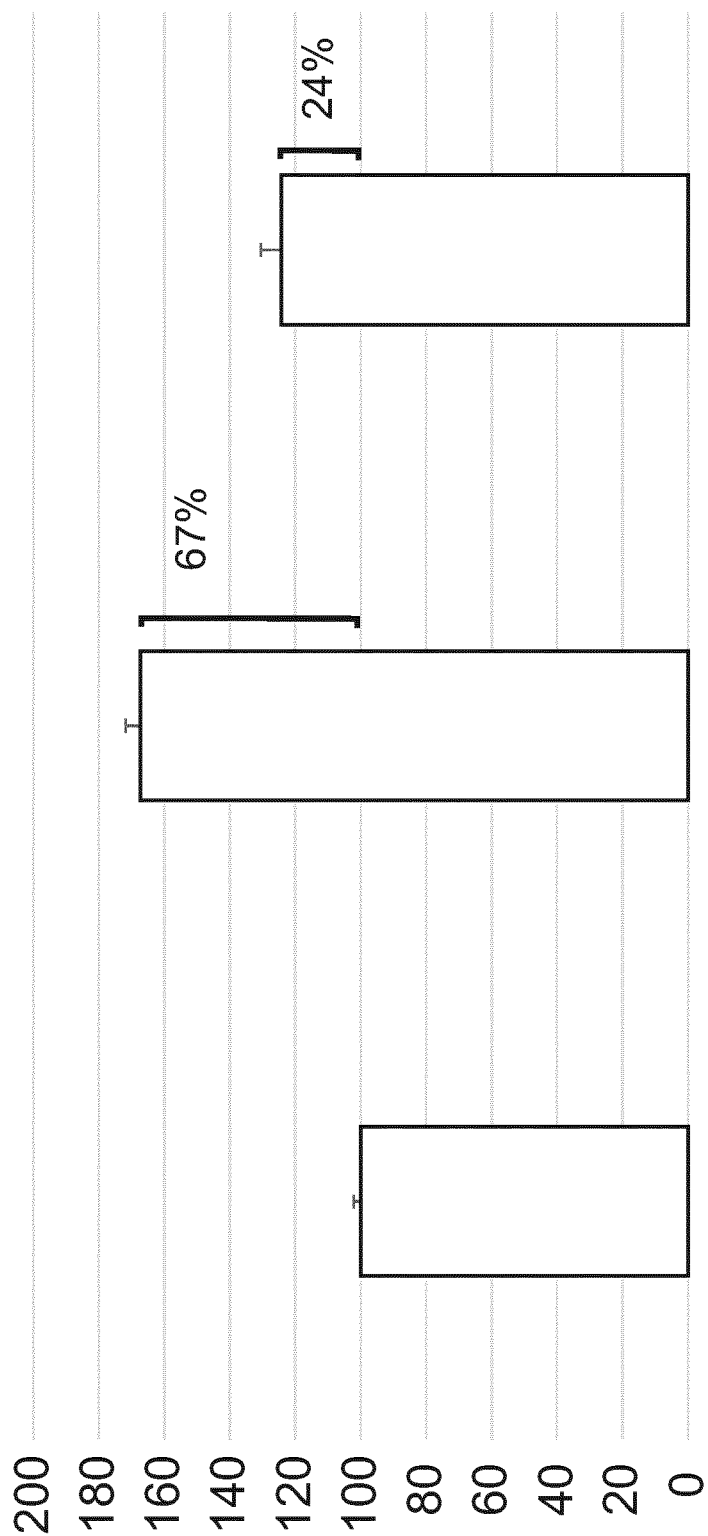

FIG. 9 shows the delay in time of exocytosis on a human neuroblastoma cell line after treatment with the peptide Ac-SEQ ID NO: 8-NH$_2$ or the benchmark acetyl hexapeptide-8 with regard to the basal control of non-treated cells which is established as 100%. Columns from left to right in the X-axis correspond to non-treated cells, 1 mg/ml of acetyl hexapeptide-8 and 0.01 mg/ml of peptide Ac-SEQ ID NO: 8-NH$_2$. The Y-axis shows the percentage of the response time corresponding to the delay of exocytosis with regard to the basal control, established at 100% level.

Figure 10A:
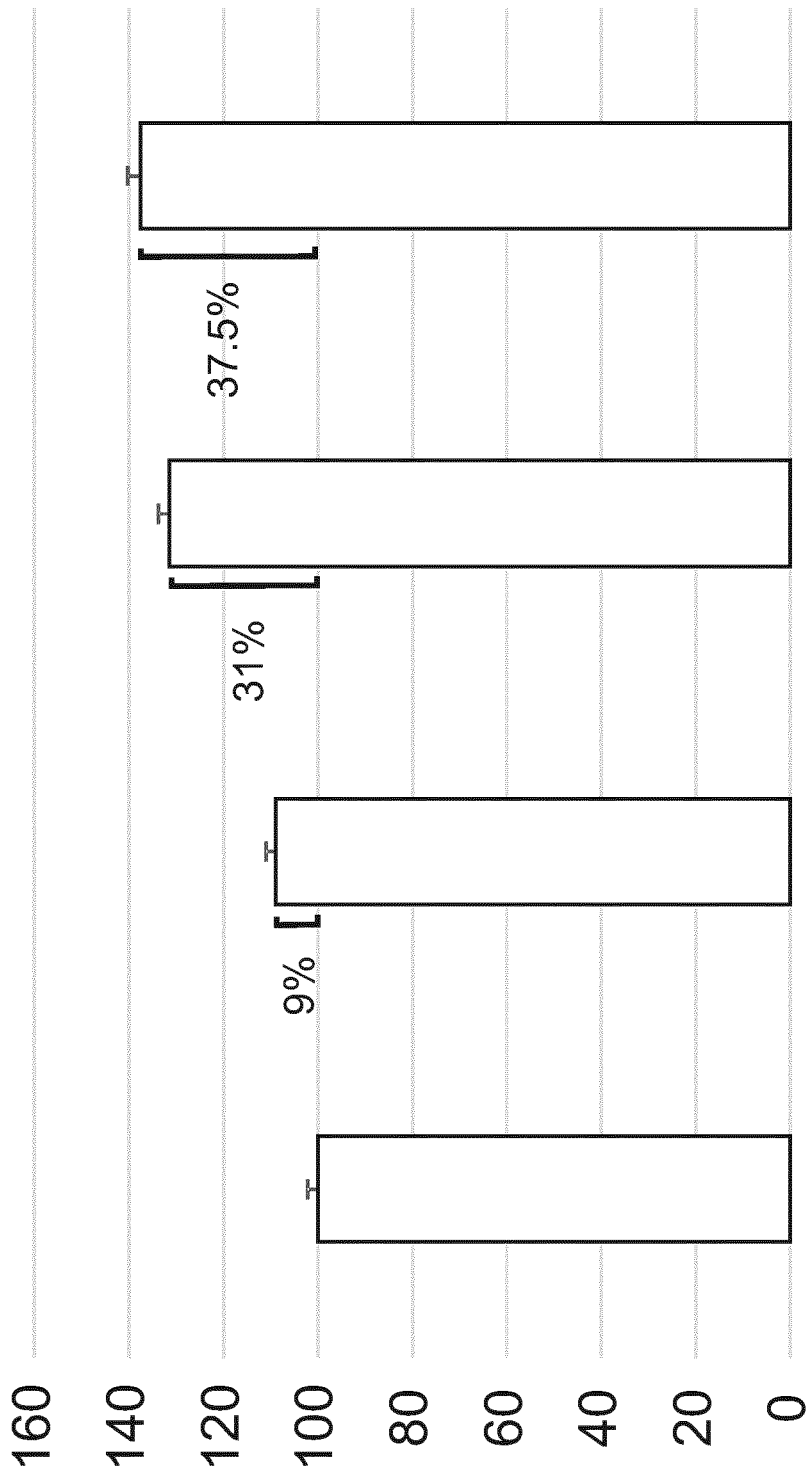
Figure 10B:
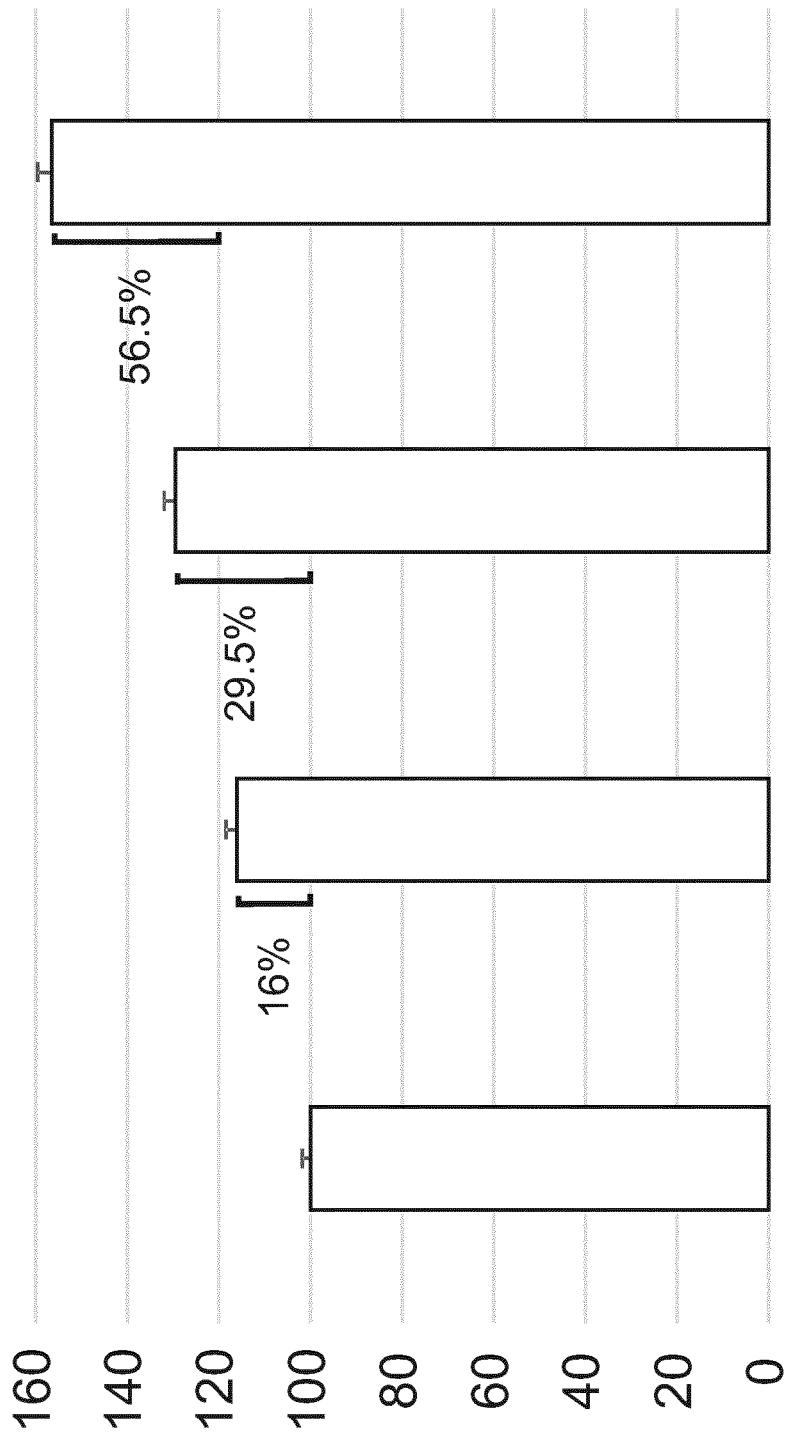

FIG. 10 shows the collagen type I production by primary human dermal fibroblasts after treatment with Ac-SEQ ID NO: 8-NH$_2$ with regard to the basal control (non-treated cells) which is established as 100%, at 24 h after the beginning of the treatment (FIG. 10(A)) and at 48 h after the beginning of the treatment (FIG. 10(B)). Columns from left to right in the X-axis correspond to: basal control (non-treated cells) and cells treated with 0.01, 0.05 or 0.1 mg/ml of peptide Ac-SEQ ID NO: 8-NH$_2$, respectively. The Y-axis shows the percentage of increase of collagen type I protein synthesis with regard to the control, established at 100% level.

EXAMPLES

Abbreviations

The abbreviations used for amino acids follow the 1983 IUPAC-IUB Joint Commission on Biochemical Nomenclature recommendations outlined in Eur. J. Biochem. (1984) 138:937.

Ac, acetyl; Ala, alanine; Arg, arginine; Asn, Asparagine; Asp, Aspartic acid; Boc, tert-butyloxycarbonyl; C-terminal, carboxy-terminal; DCM, dichloromethane; DIEA, N,N'-diisopropylethylamine; DIPCDI, N,N'-diisopropylcarbodiimide; DMF, N,N-dimethylformamide; equiv, equivalent; ESI-MS, electrospray ionization mass spectrometry; Fmoc, 9-fluorenylmethyloxycarbonyl; Glu, Glutamic acid; hiPSC, human induced pluripotent stem cells; His, histidine; HOBt, 1-hydroxybenzotriazole; HPLC, high performance liquid chromatography; HRP, Horseradish peroxidase; Ile, Isoleucine; INCI, International Nomenclature of Cosmetic Ingredients; MBHA, p-methylbenzhydrylamine; Leu, leucine; Lys, lysine; Me, methyl; MeCN, acetonitrile; MeOH, methanol; Met, Methionine; N-terminal, amino-terminal; Palm, palmitoyl; Pbf, 2,2,4,6,7-pentamethyldihydrobenzofuran-5-sulfonyl; PFA, paraformaldehyde; PMA, phorbol 12-myristate 13-acetate; Phe, Phenylalanine; PMSF, Phenylmethanesulfonyl; RT, room temperature; tBu, tert-butyl; Thr, Threonine; TFA, trifluoroacetic acid; TIS, triisopropylsilane; TMB, Tetramethylbenzidine; Trt, triphenylmethyl or trityl; Trp, Tryptophan; Tyr, Tyrosine.

Regarding the chemical synthesis procedures included in the examples, it is noted that all synthetic processes were carried out in polypropylene syringes fitted with porous polyethylene discs or Pyrex® reactors fitted with porous plates. All the reagents and solvents were synthesis quality and were used without any additional treatment. The solvents and soluble reagents were removed by suction. The Fmoc group was removed with piperidine-DMF (2:8, v/v) (at least 1×1 min, 2×10 min, 5 mL/g resin) (Lloyd Williams P. et al., Chemical Approaches to the Synthesis of Peptides and Proteins, C R C, 1997, Boca Raton (Fla., USA)). Washes between stages of deprotection, coupling, and, again, deprotection, were carried out with DMF (3×1 min) and DCM (3×1 min) each time using 10 ml solvent/g resin. Coupling reactions were performed with 3 ml solvent/g resin. The control of the couplings was performed by carrying out the ninhydrin test (Kaiser E. et al., Anal. Biochem., 1970, 34: 595598). All synthetic reactions and washes were carried out at RT.

Example 1. In Silico Determination of Peptides Interfering in the Interaction of Mync18-Syntaxin-1

In this experiment, the objective was to generate in silico peptides with affinity and/or specificity for the interaction regions of Munc18 and Syntaxin-1 and, hence, that could be able to compete, interfere and disrupt the interaction and/or binding between said two proteins.

Since the structure of Munc18-Syntaxin-1 complex was known and available at 2.6 A resolution (Protein Data Bank reference number 3C98), a three-dimensional structure model of this interaction was generated and the interaction fragments of Munc18 included in table 1 were selected.

binder peptide 0%), and all the positions were treated as independent. Each individual position was mutated to the 20 natural amino acids, while the other positions remained as Ala. The theoretical binding energy between the fragment and the rest of the complex was determined to assess the improvement of the interaction with the mutagenesis in the different positions. The t

TABLE 2-continued peptides of the in silico study selected for further study and verification.

| Sequence of the interaction fragment | Sequence of the peptide | ID of the peptide | ΔG (Joules) |
|---|---|---|---|
| 59-Glu-Asp-Ile-Asn-Lys-Arg-Arg-Glu-66 | Glu-Arg-Ile-Asn-Lys-Met-Arg-Tyr | SEQ ID NO: 14 | −8.12 |

Example 2. Synthesis and Preparation of the Peptides

Obtaining Fmoc-AA$_1$-AA$_2$-AA$_3$-AA$_4$-AA$_5$-AA$_6$-Rink-MBHA-resin, wherein AA$_1$ is L-His; AA$_2$ is L-Ile or L-Ala; AA$_3$ is L-Leu or L-Met; AA$_4$ is L-Asp or L-Arg; AA$_5$ is L-Met, L-Trp or L-Phe; and AA$_6$ is L-Trp.

Weights were normalized. 4.8 g (2.5 mmol) of the Fmoc-Rink-MBHA resin with a functionalization of 0.52 mmol/g were treated with piperidine-DMF according to the described general protocol known in the state of the art in order to remove the Fmoc group. 3.94 g of Fmoc-L-Trp(Boc)-OH (7.5 mmol; 3 equiv) were incorporated onto the deprotected resin in the presence of DIPCDI (1.17 mL; 7.5 mmol; 3 equiv) and HOBt (1.01 g; 7.5 mmol; 3 equiv) using DMF as a solvent for one hour.

The resin was then washed as described in the general methods known in the state of the art and the deprotection treatment of the Fmoc group was repeated to couple the next amino acid. Following the previously described protocols 2.90 g of Fmoc-Phe-OH, 2.78 g of Fmoc-L-Met-OH or 3.94 g of Fmoc-L-Trp(Boc)-OH (7.5 mmol; 3 equiv); subsequently 4.86 g of Fmoc-L-Arg(Pbf)-OH or 3.08 g of Fmoc-L-Asp(tBu)-OH (7.5 mmol; 3 equiv); subsequently 2.65 g of Fmoc-L-Leu-OH or 2.78 g of Fmoc-L-Met-OH (7.5 mmol; 3 equiv); subsequently 2.33 g Fmoc-L-Ala-OH or 2.65 g Fmoc-L-Ile-OH (7.5 mmol; 3 equiv) and subsequently 4.64 g of Fmoc-L-His(Trt)-OH (7.5 mmol; 3 equiv) were coupled, sequentially, each coupling in the presence of 1.01 g of HOBt (7.5 mmol; 3 equiv) and 1.17 mL of DIPCDI (7.5 mmol; 3 equiv). As already noted above, between each amino acid addition step, a deprotection treatment of the Fmoc group was performed.

After the synthesis, the peptide resins were washed with DCM (5 times for 3 minutes each one) and dried under vacuum.

Obtaining Fmoc-AA$_1$-AA$_2$-AA$_3$-AA$_4$-Rink-MBHA-Resin, Wherein AA$_1$ is L-Arg; AA$_2$ is L-Arg or L-Met; AA$_3$ is L-Arg and AA$_4$ is L-Phe.

Weights were normalized. 4.8 g (2.5 mmol) of the Fmoc-Rink-MBHA resin with a functionalization of 0.52 mmol/g were treated with piperidine-DMF according to the described general protocol of the state of the art in order to remove the Fmoc group. 2.90 g of Fmoc-L-Phe-OH (7.5 mmol; 3 equiv) were incorporated onto the deprotected resin in the presence of DIPCDI (1.17 mL; 7.5 mmol; 3 equiv) and HOBt (1.01 g; 7.5 mmol; 3 equiv) using DMF as a solvent for one hour.

The resin was then washed as described in the general methods and the deprotection treatment of the Fmoc group was repeated to couple the next amino acid. Following the previously described protocols, 4.86 g of Fmoc-L-Arg(Pbf)-OH (7.5 mmol; 3 equiv); subsequently 4.86 g of Fmoc-L-Arg(Pbf)-OH or 2.78 g of Fmoc-L-Met-OH (7.5 mmol; 3 equiv) and subsequently 4.86 g of Fmoc-L-Arg(Pbf)-OH (7.5 mmol; 3 equiv) were coupled, sequentially, each coupling in the presence of 1.01 g of HOBt (7.5 mmol; 3 equiv) and 1.17 mL of DIPCDI (7.5 mmol; 3 equiv). As already noted above, between each amino acid addition step, a deprotection treatment of the Fmoc group was performed.

After the synthesis, the peptide resins were washed with DCM (5 times for 3 minutes each one) and dried under vacuum.

Obtaining Fmoc-AA$_1$-AA$_2$-AA$_3$-AA$_4$-AA$_5$-AA$_6$-AA$_7$-AA$_8$-Rink-MBHA-Resin, Wherein AA$_1$ is L-Glu; AA$_2$ is L-Arg; AA$_3$ is L-Ile; AA$_4$ is L-Asn; AA$_5$ is L-Lys; AA$_6$ is L-Arg or L-Met; AA$_7$ is L-Arg and AA$_8$ is L-Trp or L-Tyr.

Weights were normalized. 4.8 g (2.5 mmol) of the Fmoc-Rink-MBHA resin with a functionalization of 0.52 mmol/g were treated with piperidine-DMF according to the described general protocol known in the state of the art in order to remove the Fmoc group. 3.94 g of Fmoc-L-Trp(Boc)-OH or 3.44 g of Fmoc-L-Tyr(tBu)-OH (7.5 mmol; 3 equiv) were incorporated onto the deprotected resin in the presence of DIPCDI (1.17 mL; 7.5 mmol; 3 equiv) and HOBt (1.01 g; 7.5 mmol; 3 equiv) using DMF as a solvent for one hour.

The resin was then washed as described in the general methods and the deprotection treatment of the Fmoc group was repeated to couple the next amino acid. Following the previously described protocols, 4.86 g of Fmoc-Arg(Pbf)-OH (7.5 mmol; 3 equiv); subsequently 4.86 g of Fmoc-L-Arg(Pbf)-OH or 2.78 g of Fmoc-L-Met-OH (7.5 mmol; 3 equiv); subsequently 3.51 g of Fmoc-L-Lys(Boc)-OH (7.5 mmol; 3 equiv); subsequently 4.45 g Fmoc-L-Asn(Trt)-OH (7.5 mmol; 3 equiv); subsequently 2.65 g Fmoc-L-Ile-OH; subsequently 4.86 g Fmoc-L-Arg(Pbf)-OH and subsequently 3.19 g of Fmoc-L-Glu(OtBu)-OH (7.5 mmol; 3 equiv) were coupled, sequentially, each coupling in the presence of 1.01 g of HOBt (7.5 mmol; 3 equiv) and 1.17 mL of DIPCDI (7.5 mmol; 3 equiv). As already noted above, between each amino acid addition step, a deprotection treatment of the Fmoc group was performed.

After the synthesis, the peptide resins were washed with DCM (5 times for 3 minutes each one) and dried under vacuum.

Using the synthesis procedures mentioned above, with the required selection of amino acids, the following sequences were synthesized:

```
                                      (SEQ ID NO: 5)
    His-Ile-Leu-Asp-Met-Trp;

(SEQ ID NO: 6)
    His-Ile-Met-Asp-Phe-Trp;

(SEQ ID NO: 7)
    His-Ile-Leu-Asp-Trp-Trp;

(SEQ ID NO: 8)
    His-Ala-Leu-Arg-Phe-Trp;
```

His-Ile-Met-Asp-Trp-Trp;                    (SEQ ID NO: 9)

Arg-Arg-Arg-Phe;                            (SEQ ID NO: 10)

Arg-Met-Arg-Phe;                            (SEQ ID NO: 11)

Glu-Arg-Ile-Asn-Lys-Arg-Arg-Trp;            (SEQ ID NO: 13)
and

Glu-Arg-Ile-Asn-Lys-Met-Arg-Tyr.            (SEQ ID NO: 14)

Example 3. Removal of Fmoc N-Terminal Protective Group of the Peptides Synthesized in Accordance with Example 2

The N-terminal Fmoc group of the peptidyl resins was deprotected with 20% piperidine in DMF (1×1 min+2×10 min) (Lloyd Williams P. et al. (1997) "Chemical Approaches to the Synthesis of Peptides and Proteins" CRC, Boca Raton (Fla., USA)). The peptidyl resins were washed with DMF (5×1 min), DCM (4×1 min), and dried under vacuum.

Example 4. Process for Introducing the $R_1$ Acetyl Group onto the Peptidyl Resins Obtained in Accordance with Example 3

1 mmol (1 equiv) of the peptidyl resins obtained in accordance with Example 2 was treated with 25 equivalents of acetic anhydride in the presence of 25 equivalents of DIEA using 5 mL of DMF as a solvent. They were left to react for 30 minutes, after which the peptidyl resins were washed with DMF (5×1 min), DCM (4×1 min), and were dried under vacuum.

Example 5. Cleavage Process from the Polymeric Support of the Peptidyl Resins Obtained in Accordance with Example 3 and 4

Weights were normalized. 200 mg of the dried peptidyl resin obtained in any of Examples 2, 3 or 4 were treated with 5 mL of TFA/TIS/H$_2$O (90:5:5) for 2 hours at room temperature under stirring. The filtrates were collected and precipitated using 50 mL (8 to 10-fold) of cold diethyl ether. The ethereal solutions were evaporated to dryness at reduced pressure and room temperature, the precipitates were redissolved in 50% MeCN in H$_2$O and lyophilized.

Example 6. Characterization of the Peptides Synthesized and Prepared in Accordance with Example 5

HPLC analysis of the peptides obtained in accordance with example 5 was carried out with a Shimadzu equipment (Kyoto, Japan) using a reverse-phase column (150×4.6 mm, XBridge Peptide BEH C18, 3.5 µm, Waters, USA) in gradients of MeCN (+0.036% TFA) in H$_2$O (+0.045% TFA) at a flow rate of 1.25 mL/min and detection was carried out at 220 nm. All peptides showed a purity exceeding 80%. The identity of the peptides obtained was confirmed by ESI-MS in a Water ZQ 4000 detector using MeOH as the mobile phase and a flow rate of 0.2 mL/min. Results obtained demonstrated that the peptides included in table 3 were effectively synthesized.

TABLE 3

Final peptides synthesized.

| Peptide | ID of the peptide |
| --- | --- |
| Ac-His-Ile-Leu-Asp-Met-Trp-NH$_2$ | Ac-SEQ ID NO: 5-NH$_2$ |
| Ac-His-Ile-Met-Asp-Phe-Trp-NH$_2$ | Ac-SEQ ID NO: 6-NH$_2$ |
| Ac-His-Ile-Leu-Asp-Trp-Trp-NH$_2$ | Ac-SEQ ID NO: 7-NH$_2$ |
| Ac-His-Ala-Leu-Arg-Phe-Trp-NH$_2$ | Ac-SEQ ID NO: 8-NH$_2$ |
| Ac-His-Ile-Met-Asp-Trp-Trp-NH$_2$ | Ac-SEQ ID NO: 9-NH$_2$ |
| Ac-Glu-Arg-Ile-Asn-Lys-Arg-Arg-Trp-NH$_2$ | Ac-SEQ ID NO: 13-NH$_2$ |
| Ac-Glu-Arg-Ile-Asn-Lys-Met-Arg-Tyr-NH$_2$ | Ac-SEQ ID NO: 14-NH$_2$ |
| Ac-Arg-Arg-Arg-Phe-NH$_2$ | Ac-SEQ ID NO: 10-NH$_2$ |
| Ac-Arg-Met-Arg-Phe-NH$_2$ | Ac-SEQ ID NO: 11-NH$_2$ |

Example 7. Measurement of Acetylcholine Release

The peptides included in the above table 3 were synthesized in accordance with examples 2 to 6.

Said peptides were tested for their ability to modulate acetylcholine release in vitro. To that end, LAN cells were seeded on 48-well culture plates and allowed to reach the appropriate confluence under controlled conditions (37° C., 5% CO$_2$) before inducing differentiation by replacing the culture media with Neurobasal® A media, supplemented with N-2 Supplement, GlutaMAX™, choline chloride and Leukemia Inhibition factor (GIBCO, Life technologies, MA, USA). Once the cells acquired its differentiated morphology, they were treated with the peptides mentioned above at the following concentrations for 1 hour: all peptides, except Ac-SEQ ID NO: 8-NH$_2$, at 0.001 mg/mL, 0.005 mg/mL and 0.01 mg/mL; and peptide Ac-SEQ ID NO: 8-NH$_2$ at 0.005 mg/mL and 0.05 mg/mL. Cells were then washed with HEPES, before stimulation of acetylcholine release by depolarization with external 50 mM KCl solution. Non-stimulated cells were incubated with non-depolarizing 4 mM KCl solution. After 30 minutes of incubation with the corresponding depolarizing or non-depolarizing KCl solution, cell supernatants were collected and used to measure acetylcholine levels with Amplex Red Acetylcholine Assay Kit (ThermoFisher Scientific, MA, USA). Cell pellets were used to determine protein content by BCA Protein Test Assay (Pierce BCA Protein Assay kit, ThermoFisher Scientific, MA, USA) (for data normalization purposes).

Percentage of acetylcholine release inhibition was calculated considering 100% release for the positive control (non-treated stimulated with KCl cells).

The results obtained appear summarized in table 4:

TABLE 4

Summary of the results obtained in Example 7.

| Peptide | Result |
| --- | --- |
| Ac-SEQ ID NO: 5-NH$_2$ | Active in the modulation of acetylcholine release. |
| Ac-SEQ ID NO: 6-NH$_2$ | Active in the modulation of acetylcholine release. |

TABLE 4-continued

Summary of the results obtained in Example 7.

| Peptide | Result |
|---|---|
| Ac-SEQ ID NO: 7-NH$_2$ | Active in the modulation of acetylcholine release. |
| Ac-SEQ ID NO: 8-NH$_2$ | Active in the modulation of acetylcholine release. |
| Ac-SEQ ID NO: 9-NH$_2$ | Active in the modulation of acetylcholine release. |
| Ac-SEQ ID NO: 10-NH$_2$ | Active in the modulation of acetylcholine release. |
| Ac-SEQ ID NO: 11-NH$_2$ | Active in the modulation of acetylcholine release. |
| Ac-SEQ ID NO: 13-NH$_2$ | Non-active in the modulation of acetylcholine release. |
| Ac-SEQ ID NO: 14-NH$_2$ | Non-active in the modulation of acetylcholine release. |

The results of this experiment also appear summarized in FIG. 1 (A) to (I). As can be directly derived from said figures, the peptides marked as active in the modulation of acetylcholine in table 4, show a significant decrease in the release of acetylcholine in all the concentrations tested. On the other side, peptides marked as non-active in table 4 show a moderate-to-low inhibition at the lowest concentrations and complete loss of inhibition at the highest concentration. Said peptides did not show a statistical decrease in the release of acetylcholine in any of the concentrations tested. The fact that at low concentrations a slight inhibition was observed was expected due to the technical complication of this type of cells and the inherent variability of the test, but the complete loss of activity at the highest concentration clearly shows these peptides (Ac-SEQ ID NO: 13-NH$_2$ and Ac-SEQ ID NO: 14-NH$_2$) were not able to inhibit the release of acetylcholine.

As seen from prior art (Blanes-Mira C., Clemente J., Jodas G., et.al. (2002), *A synthetic hexapeptide (Argireline) with antiwrinkle activity*, International Journal of Cosmetic Science, 24, 303-310), the inhibition of exocytosis from permeabilized chromaffin cells reached maximum values of 50% when using BoNT A or 40% when using Argireline®. Therefore, the results obtained in this example prove the high activity of the peptides of the present invention as when testing the inhibition of acetylcholine release directly on LAN cells, not even permeabilized, values of 20-30% of inhibition were obtained Example 8. Binding Assay The following peptides were synthesized based on the in silico study of example 1 and in accordance with examples 2 to 6:
Ac-SEQ ID NO: 5-NH$_2$
Ac-SEQ ID NO: 8-NH$_2$ The capacity of the peptides to inhibit Munc18 protein-protein interaction with Syntaxin-1, a SNARE complex protein, was functionally evaluated by means of an ELISA-based in vitro Munc18/Syntaxin-1 binding assay. Briefly, the above-mentioned peptides at 0.1, 0.5 and 1 mM were preincubated with their target protein Syntaxin-1 (GST-tagged) at 10 and 5 nM in buffer (20 mM Hepes, 150 mM NaCl, 2 mM $MgC_2$, 2 mM DTT, 0.5% Triton-X100 and 0.5% non-fat milk) for 3 hours at RT. Meanwhile, His-tagged Munc18 was bound to a Nickel-coated 96-well plate at 100 nM and incubated at RT for 1.5 hours. Non-bound protein was subsequently washed away before blocking wells with non-fat milk in wash buffer (PBS+0.02% Triton-X100) for additional 30 minutes. GST-tagged Syntaxin-1 preincubated with the peptides was then added at 10 and 5 nM to the plate and incubated for 2 h at RT. Wells were washed three times with wash buffer before incubation with the primary antibody (GST tag polyclonal antibody—Thermofisher Scientific, Massachusetts, USA) for 45 minutes. Finally, after washing again, HRP-conjugated secondary antibody (Anti-Rabbit-IgG-HRP—Sigma, Missouri, USA) was added and incubated at RT. TMB substrate (3,3',5,5'-Tetramethylbenzidine) was used to develop signal. Reaction was stopped by addition of Stop Reagent. Amount of binding of Syntaxin-1 protein to Munc18 protein was analysed by measuring absorbance at 450 nm.

The results obtained in this experiment appear summarized in FIG. 2. FIG. 2 evidences that both peptides tested (Ac-SEQ ID NO: 5-$NH_2$ to an even surprisingly higher degree), were able to significantly block protein-protein interactions between Munc18 and Syntaxin-1, showing even a dose-response manner. Maximum inhibition reached 37% and 67% for Ac-SEQ ID NO: 8-$NH_2$ and Ac-SEQ ID NO: 5-$NH_2$ peptides, respectively. Based in these results, it can be seen that the peptides of the present invention are able to disrupt the protein-protein interaction required for regulated exocytosis and consequent neurotransmitter release.

Example 9. Gene Expression Modulation in Skeletal Muscle Human Myocytes

The following peptides were synthesized based on the in silico study of example 1 and in accordance with examples 2 to 6:

Ac-SEQ ID NO: 5-$NH_2$
Ac-SEQ ID NO: 8-$NH_2$
Ac-SEQ ID NO: 10-$NH_2$

Said peptides were tested to evaluate their capacity to modulate the expression of several genes related with muscle contraction and relaxation in human skeletal muscle myocytes (Lodish H, Berk A, Zipursky S L, et al. (2000), *Molecular Cell Biology,* 4th edition; Section 18.3 Myosin: The Actin Motor Protein, Nueva York, W. H. Freeman; Kuo, I Y, & Ehrlich, B E (2015), *Signaling in Muscle Contraction*, Cold Spring Harbor Perspectives in Biology, 7(2); RAPSN receptor associated protein of the synapse [*Homo sapiens* (human)], Gene ID in NCBI 5913; Blake D J, Tinsley J M, Davies K E (1996), *Utrophin: a structural and functional comparison to dystrophin*, Brain Pathol., 6(1):37-47; Barik A, Lu Y, Sathyamurthy A, et.al. (2014), *LRP4Is Critical for Neuromuscular Junction Maintenance*, The Journal of Neuroscience, 34(42), 13892-13905; Kim N, Stiegler A L, Cameron T O, Hallock P T, et.al. (2008), *Lrp4 is a Receptor for Agrin and Forms a Complex with MuSK*, Cell, 135(2), 334-342; Mahavadi S, Nalli A, Kumar D, et.al. (2014), *Increased expression of caveolin-1 is associated with upregulation of the RhoA/Rho kinase pathway and smooth muscle contraction in diabetes* (1110.11), The FASEB Journal, 28:1_supplement)). To that end, a contractility smart data gene panel was designed. Said contractility smart data gene panel analyses the expression of the genes related with muscular contraction and relaxation included in table 5.

TABLE 5

| Genes analyzed in example 9. | |
|---|---|
| Symbol | Gene name |
| MYH1 | Myosin Heavy Chain |
| SCN3A | Sodium Voltage-Gated Channel Alpha Subunit 3 |

TABLE 5-continued

Genes analyzed in example 9.

| Symbol | Gene name |
|---|---|
| RAPSN | Receptor Associated protein of the Synapse |
| TNNC 1 | Troponin C1 |
| ACTA 1 | Actin |
| UTRN | Utrophin |
| CACNB1 | Calcium Voltage-Gated channel Auxiliary Subunit Beta 1 |
| CHRNA1 | Nicotinic Acetylcholine Receptor Alpha Subunit 1 |
| CALM3 | Calmodulin 3 |
| CAV1 | Caveolin 1 |
| LRP4 | LDL Receptor Related Protein 4 |

Briefly, human skeletal muscle myoblasts were seeded in duplicate in 12-well culture plates at a density of 1×10⁵ cells/well and maintained at standard culture conditions (37° C., 95% humidity, 5% $CO_2$) for 48-72h. Myoblast differentiation to myocyte was then induced with specific differentiation media (SKM-D medium+1% Antibiotic-Antimycotic) and monitored for 7 more days. Differentiated cells were treated with 0.05 mg/mL of peptide Ac-SEQ ID NO: 5-$NH_2$; or with 0.1 mg/mL of peptide Ac-SEQ ID NO: 10-$NH_2$ for 24 hours; or with 0.05 and 0.5 mg/mL of peptide Ac-SEQ ID NO: 8-$NH_2$ for 6h; or with 0.5 mg/mL of peptide Ac-SEQ ID NO: 8-$NH_2$ for 24 h. Untreated cells were used as basal control. Cells were then lysed for RNA extraction with a RNA purification commercial kit following manufacturer instructions (RNeasy mini kit, Qiagen, Netherlands). RNA was then quantified by nanodrop, adjusted in concentration and processed for retrotranscription to cDNA using a commercially available kit (High-Capacity cDNA Reverse Transcription kit, Thermofisher Scientific, USA). Resulting cDNA was used to perform a RTqPCR (Real Time Quantitative Polymerase Chain Reaction) using taqman technology and a panel of probes designed to target the specific genes related to muscle contractility mentioned in table 4.

The results of this experiment appear summarized in FIG. 3(A) to (D). In said figures it can be seen that when human myocytes were treated with peptide Ac-SEQ ID NO: 5-$NH_2$ a downregulation of UTRN, ACTA1, TNNC1, RAPSN, SCN3A and MYH1 was observed. Treatment of myocytes with peptide Ac-SEQ ID NO: 8-$NH_2$ resulted in a downregulation of SCN3A, UTRN, ACTA1, TNNC1, CALM3, CAV1, CACNB1, LRP4, and MYH1 for the 6-hour treatment, together with a downregulation of RAPSN and an upregulation of ATP2A for the 24-hour treatment. Finally, treatment of myocytes with peptide Ac-SEQ ID NO: 10-$NH_2$ resulted in a downregulation of UTRN, TNNC1, SCN3A CHRNA1 and CACNB1.

Downregulation of the above-mentioned genes may affect normal muscle contractility function in different ways: RAPSN, CHRNA1, UTRN and LRP4, required for the binding of acetylcholine on the surface of the muscle cell, may affect neurotransmitter-induced membrane depolarization and cytoskeleton stability; SCN3A and CACNB1, as voltage-gated channels, may affect membrane potential an excitation transmission; SLN, involved in $Ca^{2+}$ transportation, may affect intracellular calcium accumulation; and MYH1, TNNC1 and ACTA1 may affect cytoskeleton integrity and the power strike that drives contraction. Therefore, the results obtained in this example and shown in FIG. 3, demonstrate the ability of the peptides of the present invention to modulate muscular contraction-relaxation, contributing to an increase in the relaxation of muscles.

Example 10. Calcium Mobilization Assay

Peptide Ac-SEQ ID NO: 8-$NH_2$ was synthesized in accordance with examples 2 to 6.

The potential of said peptide Ac-SEQ ID NO: 8-$NH_2$ to reduce calcium mobilization on human skeletal muscle cells was evaluated in vitro with Fluo-4 NW Calcium Assay Kit (ThermoFisher Scientific, MA USA). Briefly, human skeletal muscle myoblasts were seeded in quintuplicates in a black 96-well plate, clear bottom, at a density of 1×10⁴ cells/well and maintained at standard culture conditions (37° C., 95% humidity, 5% $CO_2$) for 48-72h. Myoblast differentiation to myocyte was then induced with specific differentiation medium (SKM-D medium+1% a/a) and monitored for 7 more days. Differentiated cells were treated with non-cytotoxic concentrations of peptide Ac-SEQ ID NO: 8-$NH_2$ (0.01 mg/mL, 0.05 mg/mL and 0.1 mg/mL) for additional 48 hours.

Once incubation was finished, cell culture medium was replaced by 100 µl of Dye loading solution and the plate was kept on the incubator for 30 minutes. Dye solution was then replaced by assay buffer prior to calcium measurement using FLUOstar Omega instrument (BMG Labtech, Germany). For appropriate kinetic measurement, a pre-stimulus phase of 10 seconds was set to determine the baseline signal before induction of calcium influx by addition of 60 mM KCl. Post-stimulus phase was set at 90 seconds, with readings every 0.1 seconds at 494/516 nm (excitation/emission).

The following steps were performed for data analysis: 1) Calculation of a mean kinetic curve for each condition; 2) determination of maximum fluorescent signal for each curve after stimulation with KCl; 3) calculation of the fold change increase versus baseline; 4) normalization of results obtained for each condition (each peptide concentration) versus the one obtained for the control (untreated cells).

The results obtained in this experiment appear summarized in FIG. 4 and reflect the potential of the peptides of the present invention (as exemplified by Ac-SEQ ID NO: 8-$NH_2$) to reduce calcium influx in a dose dependent manner (−6%, −20% and −30% at 0.01 mg/mL, 0.05 mg/mL and 0.1 mg/mL respectively). This reduction in calcium influx has an impact on cell contractility favoring muscle relaxation.

As can be directly derived from the above examples, the peptides of the present invention effectively interfere or inhibit the formation of the complex Munc18-Syntaxin-1, hence, allowing a regulation (inhibition) of neuronal exocytosis. In addition, said peptides provide a direct effect on muscle cells inducing or contributing to their relaxation (muscle relaxation). Therefore, the peptides of the present invention solve the above-mentioned problems present in the state of the art.

Example 11. Myosin Heavy Chain Protein Decrease

The potential of said peptide Ac-SEQ ID NO: 8-$NH_2$ to decrease the expression of the protein myosin heavy chain in human skeletal muscle cells was evaluated in vitro by immunofluorescence using a specific antibody against this protein (Biotechne, USA) followed by a secondary fluorescent antibody (Thermofisher, USA). Briefly, human skeletal muscle myoblasts were seeded onto coverslips in SKM-M medium (Tebu-Bio, France) at a density of 3×10⁴ cells/cm² and incubated overnight at standard culture conditions (37° C., 95% humidity, 5% $CO_2$). Myoblast differentiation to myocyte was then induced with specific differentiation medium (Skeletal Muscle Cell Differentiation Medium, SKM-D medium) and monitored for 7 more days. Differentiated cells were treated with non-cytotoxic concentrations of peptide Ac-SEQ ID NO: 8-$NH_2$ (0.05 mg/mL and 0.5 mg/mL) for additional 48 hours.

Once incubation was finished, cells were fixed with 4% PFA and permeabilized using 0.1% (v/v) Triton (Sigma, USA). Myosin was then stained with 0.5 mg/ml myosin heavy chain antibody during 2 h at room temperature. After proper washing, actin protein was labelled with 50 µg/ml Phalloidin (red) (Sigma, USA) for 1 h and, after washing, cells were stained with 4 µg/ml of the secondary antibody Goat anti-Mouse IgG for 1 h. Finally, nuclei were stained with 3.5 µg/ml Hoescht marker for 10 min (Sigma, USA).

Microscopic images were acquired using the 5× and 10× objectives. Three replicates were used for each condition and images of three to four fields of each coverslip were acquired using the same settings.

Images were analyzed using Image J software. Shortly, threshold was adjusted to select myosin and mean fluorescent was measured. The number of positive cells was counted using DAPI staining. Myosin mean fluorescent intensity was divided by the number of myosin-positive cells. Finally, all data was normalized as follows to obtain the % of myosin compared to non-treated cells: % vs. control=(fluorescence per cell in treated wells/fluorescence per cell in non-treated wells)×100.

The results obtained in this experiment appear summarized in FIGS. 5(A), 5(B) and 6 and reflect the potential of the peptides of the present invention (as exemplified by Ac-SEQ ID NO: 8-$NH_2$) to reduce myosin heavy chain protein levels in a dose dependent manner (−26% and −38% at 0.05 mg/mL and 0.5 mg/mL in FIG. 6, respectively). This reduction in myosin heavy chain protein levels has an impact on cell contractility favoring muscle relaxation.

As can be directly derived from the above example, the peptides of the present invention effectively provide a direct effect on muscle cells inducing or contributing to their relaxation (muscle relaxation).

Example 12. Contraction Frequency

The potential of said peptide Ac-SEQ ID NO: 8-$NH_2$ to modulate the contraction frequency was evaluated in vitro using human muscle cells and motor neurons derived from hiPSC co-cultures, by means of live-imaging video of localized contractile muscle fibers recorded with an InCell 2200 automated microscope during 60 seconds, before and after treatment (after treatment, at each of the established time-points).

Human muscle cells were cultivated at a density of $1 \times 10^6$ cells in T75 $cm^2$ flasks and then transferred to 96 well plates for differentiation. Motor neurons derived from hiPSC were transferred onto the 96 well plates containing the muscle cells in a differentiation medium. Co-cultures were maintained for 10 days in order to generate neurons junctions with muscle fibers. Spontaneous contractions were observed within 5 days.

Co-cultures were then treated with control medium (basal), 1 µM α-bungarotoxin, 0.5 mg/mL of acetyl hexapeptide-8 as a benchmark reference and 0.05 or 0.1 mg/mL of peptide Ac-SEQ ID NO: 8-$NH_2$. Movies of co-cultures were recorded during 60 seconds before treatment and, after 30 minutes of incubation, movies were recorded again during 60 seconds. The culture plate was incubated again for 1 h 30 min with compounds (2 h of total incubation), and movies of co-cultures were recorded again during 60 seconds. The culture plate was incubated again for a total of 24 h with compounds and at the end of the incubation movies were recorded again during 60 seconds. Finally, compounds were washed out and a last recording after 24 h from said washed out of the compounds was done to assess an eventual recovery of muscle contractions (recovery).

Frequencies of contraction were calculated before and after each incubation. For each culture condition, 6 wells were analyzed.

The results obtained in this experiment appear summarized in FIG. 7 and reflect the potential of the peptides of the present invention (as exemplified by Ac-SEQ ID NO: 8-$NH_2$) to induce and important dose-dependent decrease of muscles contraction frequency after only 30 min (25% and 18% of muscle contraction frequency with regard to the basal non-treated cells, at 0.05 and 0.1 mg/mL, respectively) which is maintained during the 24 h incubation period (23% and 10% at 0.05 and 0.1 mg/mL, respectively). The washout of this compound allows a partial recovery of the muscle contraction frequency which is better at 0.05 mg/mL concentration (65% and 35% at 0.05 and 0.1 mg/mL, respectively).

The benchmark (acetyl hexapeptide-8) used at 0.5 mg/mL induced a partial inhibition of muscle contraction frequency after 30 min (18% muscle contraction frequency) but this effect was attenuated with longer incubations (45% after 24 h) and after a washout, the frequency was totally restored (100%).

As can be directly derived from the above example, the peptides of the present invention effectively provide a direct effect on muscle contraction during neurons junctions formation with muscle fibers, contributing to their relaxation (muscle relaxation).

Example 13. Exocytosis Levels and Delay

The potential of said peptide Ac-SEQ ID NO: 8-$NH_2$ to modulate the exocytosis of vesicles containing neurotransmitters from a neuroblastoma cell line was evaluated in vitro using SH-SY5Y cells, by fluorescence imaging using a Zeiss axiovert 200 inverted epifluorescence microscope with a 20× objective and a Xenon lamp.

SH-SY5Y cells (Sigma, USA) were cultured in T25 flasks in supplemented medium (DMEM/F12, Gibco, USA). Above 90% confluence, cells were trypsinized with 1 ml of 0.5% (v/v) Trypsin-EDTA. Next, 5 mL of said supplemented medium was added and cell concentration determined. Cells were seeded onto polyLysine-coated 12 mm-treated coverslips in 24 well-plates at $15 \times 10^4$ cells/well in supplemented medium (Gibco, USA) and incubated at regular conditions (37° C., 5% $CO_2$). After 24 h cell seeding, cells were transfected with exocytosis reporter using Lipofectamine™ 3000 (Invitrogen, USA) following manufacturer's instructions. Reporter construct contained fusion protein made up of intraluminal-specific proteins and a pH-sensitive fluorescent protein.

For exocytosis monitorization, after 48 h of protein expression, cells were incubated with 0.01 mg/mL of Ac-SEQ ID NO: 8-$NH_2$ peptide or 1 mg/mL of the benchmark acetyl hexapeptide-8 for 1 h at 37° C. and 5% $CO_2$. Non-treated cells were used as basal control. Then, cells were pre-treated with 100 nM PMA for 15 min and stimulated with 12.5 µM ionomycin together with PMA (100 nM) for 5 minutes (total stimulation: 20 min). Fluorescence imaging was done for the last 10 min of the stimulation protocol. Fluorescence signal of exocytosis reporter was monitored employing 483-512 nm excitation-filter and 525-530 nm emission-filter. Images were captured with ORCA-ER CCD camera every 5 seconds for 10 min using Aquacosmos software.

Non-treated cells were assayed in N=4 independent experiments with n=16 coverslips (483 cells measured), acetyl hexapeptide-8-treated cells in N=3 independent experiments with n=10 coverslips (328 cells measured) and Ac-SEQ ID NO: 8-NH$_2$-treated cells in N=3 independent experiments with n=8 coverslips (240 cells measured). Cells were selected to individually monitor fluorescence intensity and time-course. Fluorescence peak evoked by ionomycin addition was used to quantify exocytosis by calculating the Area under the curve (AUC) using GraphPad software. Two parameters were defined and analyzed:

Exocytosis levels: For individual cells, total peak area was obtained from AUC analysis and was normalized by the baseline that was defined as fluorescence intensity 3-cycles before Ionomycin injection.

Exocytosis delay: For individual cells, response time (min) was obtained from AUC analysis as time frame between Ionomycin injection (Y) and initiation of peak (firstX).

Fluorescence values were further normalized as percentage change to non-treated cells on each experiment as: (exocytosis level of treated cells/exocytosis levels non-treated cells)×100 and (response time of treated cells/response time of non-treated cells)×100.

For analysis of exocytosis monitorization parameters: Data represent percentages normalized to non-treated cells for exocytosis levels and exocytosis delay. Data are expressed as mean±SEM; Data was obtained from N=4 independent experiments, n=16 replicates (483 cells measured) for non-treated cells; N=3 independent experiments, n=10 replicates for acetyl-hexapeptide-8 (328 cells measured); N=3 independent experiments, n=8 replicates (240 cells measured) for Ac-SEQ ID NO: 8-NH$_2$.

The results obtained in this experiment appear summarized in FIGS. 8 and 9 and reflect the potential of the peptides of the present invention (as exemplified by Ac-SEQ ID NO: 8-NH$_2$) to reduce (FIG. 8) and delay (FIG. 9) the exocytosis of vesicles containing acetylcholine released by neurons that activate muscle contractions through specific acetylcholine receptors.

Ac-SEQ ID NO: 8-NH$_2$ incubated for 1 hour at 0.01 mg/mL significantly delayed exocytosis response time (24% delay) and decreased exocytosis levels (−14%), while acetyl hexapeptide-8 incubated for 1 hour at 1 mg/mL significantly delayed exocytosis response (67% delay) without altering exocytosis level (7%) in human neuroblastoma cell line SH-SY5Y.

As can be directly derived from the above example, the peptides of the present invention effectively provide an indirect effect on muscle contraction by reducing the level of acetylcholine vesicles released by neurons to the synaptic space for muscle contraction and delaying said exocytosis.

Example 14. Collagen Production

The potential of said peptide Ac-SEQ ID NO: 8-NH$_2$ to modulate the production of collagen type I as a potential improver of skin firming was evaluated in vitro using human skin fibroblasts.

Cell were seeded in 96-well plates at 1×10$^4$ cells/well and maintained for 24 h at standard culture conditions (37° C., 95% humidity, 5% CO$_2$). After 24 h incubation, medium was removed and new medium containing the peptide Ac-SEQ ID NO: 8-NH$_2$ at 0.01, 0.05 or 0.1 mg/mL was added to the wells concentration. Treatment lasted 24 hours or 48 hours and at the end of the assay cell culture media were collected. Cells treated only with culture medium were used as basal control (non-treated cells).

After 24 and 48 hours of treatment the amount of collagen type I produced and released by the cells (ex-novo collagen type I synthesis) was measured in cell culture medium by means of ELISA assay. The results of the test item were compared to basal control condition (non-treated cells). The treatments were performed in triplicate in three different experimental sessions.

The determination of collagen type I synthesis was carried out by means of a competitive ELISA method. Samples were added to enzyme wells which were pre-coated with antibodies, then the recognition antigen labeled with Horseradish peroxidase (HRP) was added; after being incubated 1 hour at 37° C., both compete with solid phase antigen and form immune complex. After washing with phosphate buffer solution, the combined HRP catalyzes Tetramethylbenzidine (TMB) into blue, and turns into yellow by the action of acid; it has an absorption peak under 450 nm wavelength and its absorbance is negatively correlated with antigen density of sample. The plates were read by microplate reader.

The quantitative determination uses a calibration curve made-up of known and growing concentrations of standard collagen type 1. The results are expressed as collagen type I concentration (µg/ml) in 50 µL cell culture medium.

Three trials were performed for each determination in three different experimental sessions. The % variation in collagen type I content between negative controls and samples was calculated and a direct index of the efficacy of the peptide to increase collagen I synthesis was obtained.

The results obtained in this experiment appear summarized in FIGS. 10(A) and 10(B) and reflect the potential of the peptides of the present invention (as exemplified by Ac-SEQ ID NO: 8-NH$_2$) to induce the production of collagen type I by human dermal fibroblasts.

Ac-SEQ ID NO: 8-NH$_2$ peptide significantly boosted collagen type I production by fibroblasts after 24 h by 9%, 31% and 37.5% at 0.01, 0.05 and 0.1 mg/mL, respectively and after 48 h by 16%, 29.5% and 56.5% at 0.01, 0.05 and 0.1 mg/mL, respectively.

As can be directly derived from the above example, the peptides of the present invention effectively provide a strong effect and improving the firmness and the quality of the skin.

The invention claimed is:

1. A method of reducing skin aging and/or facial expression lines in a subject in need thereof comprising applying to the subject in need thereof a peptide or cosmetic composition comprising said peptide, wherein the peptide has a sequence in accordance with formula (I):

$$R_1\text{-}AA_1\text{-}AA_2\text{-}AA_3\text{-}AA_4\text{-}AA_5\text{-}AA_6\text{-}R_2 \quad (I)$$

cosmetically and pharmaceutically acceptable isomers, salts, solvates and/or derivatives and mixtures thereof, wherein:
$AA_1$ is His;
$AA_2$ is selected from the group consisting of Gly, Ala, Val, Leu, Met and Ile;
$AA_3$ is selected from the group consisting of Gly, Ala, Val, Leu, Met and Ile;
$AA_4$ is selected from the group consisting of Lys, Arg, His, Asp and Glu;
$AA_5$ is selected from the group consisting of Met, Phe, Tyr and Trp; and
$AA_6$ is Trp;
$R_1$ is selected from the group consisting of H, substituted or unsubstituted non-cyclic aliphatic, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO— wherein $R_5$ is selected from the group formed by substituted or unsubstituted $C_1$-$C_{24}$ alkyl radical, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_8$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl ring of 3 to 10 members, and substituted or unsubstituted heteroarylalkyl of 2 to 24 carbon atoms and 1 to 3 atoms other than carbon and an alkyl chain of 1 to 6 carbon atoms; and
$R_2$ is selected from the group consisting of H, —NR$_3$R$_4$—, —OR$_3$ and —SR$_3$, wherein R$_3$ and R$_4$ are independently selected from H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl ($R_1$-SEQ ID NO: 15-$R_2$), wherein the peptide interferes in the Munc18-Syntaxin-1 complex interaction and competes with SEQ ID NO: 3 and/or SEQ ID NO: 4, acceptable isomers, salts, solvates and/or derivatives and/or mixtures thereof.

2. The method in accordance with claim 1, wherein the peptide of formula (I) is:

(Ac-SEQ ID NO: 5-NH$_2$)
Ac-His-Ile-Leu-Asp-Met-Trp-NH$_2$;

(Ac-SEQ ID NO: 6-NH$_2$)
Ac-His-Ile-Met-Asp-Phe-Trp-NH$_2$;

(Ac-SEQ ID NO: 7-NH$_2$)
Ac-His-Ile-Leu-Asp-Trp-Trp-NH$_2$;

(Ac-SEQ ID NO: 8-NH$_2$)
Ac-His-Ala-Leu-Arg-Phe-Trp-NH$_2$;
and/or (Ac-SEQ ID NO: 9-NH$_2$)
Ac-His-Ile-Met-Asp-Trp-Trp-NH$_2$.

3. A method of reducing skin aging and/or facial expression lines in a subject in need thereof comprising applying to the subject in need thereof a peptide or cosmetic composition comprising said peptide, the peptide having a sequence in accordance with formula (II) $R_1$-$AA_1$-$AA_2$-$AA_3$-$AA_4$-$R_2$, wherein the peptide of formula (II) is:

(Ac-SEQ ID NO: 10-NH$_2$)
Ac-Arg-Arg-Arg-Phe-NH$_2$;
and/or (Ac-SEQ ID NO: 11-NH$_2$)
Ac-Arg-Met-Arg-Phe-NH$_2$.

4. The method in accordance with claim 1, wherein
$AA_1$ is His;
$AA_2$ is selected from the group of Ala and Ile;
$AA_3$ is selected from the group of Leu and Met;
$AA_4$ is selected from the group of Arg and Asp;
$AA_5$ is selected from the group of Met, Phe and Trp; and
$AA_6$ is Trp.

5. The method in accordance with claim 1, wherein the peptide of formula (I) is $R_1$-His-Ile-Leu-Asp-Met-Trp-$R_2$; ($R_1$-SEQ ID NO: 5-$R_2$)

$R_1$-His-Ile-Met-Asp-Phe-Trp-$R_2$; ($R_1$-SEQ ID NO: 6-$R_2$)

$R_1$-His-Ile-Leu-Asp-Trp-Trp-$R_2$; ($R_1$-SEQ ID NO: 7-$R_2$)

$R_1$-His-Ala-Leu-Arg-Phe-Trp-$R_2$; ($R_1$-SEQ ID NO: 8-$R_2$)
and/or $R_1$-His-Ile-Met-Asp-Trp-Trp-$R_2$. ($R_1$-SEQ ID NO: 9-$R_2$)

6. A method of reducing skin aging and/or facial expression lines in a subject in need thereof comprising applying to the subject in need thereof a peptide or cosmetic composition comprising said peptide, wherein the peptide has a sequence in accordance with formula (II) $R_1$-AA1-$AA_2$-$AA_3$-$AA_4$-$R_2$, wherein the peptide of formula (II) is $R_1$-Arg-Arg-Arg-Phe-$R_2$ ($R_1$-SEQ ID NO: 10-$R_2$); or $R_1$-Arg-Met-Arg-Phe-$R_2$ ($R_1$-SEQ ID NO: 11-$R_2$) and wherein $R_1$ is selected from the group consisting of H, substituted or unsubstituted non-cyclic aliphatic, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO— wherein $R_5$ is selected from the group formed by substituted or unsubstituted $C_1$-$C_{24}$ alkyl radical, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted Cs-$C_{24}$ cycloalkenyl, substituted or unsubstituted Cs-$C_{24}$ cycloalkynyl, substituted or unsubstituted $C_6$-$C_3O$ aryl, substituted or unsubstituted C-$C_{24}$ aralkyl, substituted or unsubstituted heterocyclyl ring of 3 to 10 members, and substituted or unsubstituted heteroarylalkyl of 2 to 24 carbon atoms and 1 to 3 atoms other than carbon and an alkyl chain of 1 to 6 carbon atoms; and $R_2$ is selected from the group consisting of H, —$NR_3R_4$—, —$OR_3$ and —$SR_3$, wherein $R_3$ and $R_4$ are independently selected from H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl ($R_1$-SEQ ID NO: 15-$R_2$).

7. The method in accordance with claim 1, wherein the skin aging and/or facial expression line being reduced are facial wrinkles and facial asymmetry.

8. The method in accordance with claim 1, wherein the cosmetic composition is applied by means of iontophoresis.

9. The method in accordance with claim 1, wherein the cosmetic composition is applied by subcutaneous injection.

10. The method in accordance with claim 1, wherein the cosmetic composition is applied topically.

11. The method in accordance with claim 1, wherein the cosmetic composition comprises the peptide at a concentration of 0.0001%-0.05% (m/v).

12. The method in accordance with claim 1, wherein the subject in need thereof is a mammal.

13. The method in accordance with claim 12, wherein the mammal is a human.

14. The method in accordance with claim 3, wherein the cosmetic composition is applied by means of iontophoresis.

15. The method in accordance with claim 3, wherein the cosmetic composition is applied by subcutaneous injection.

16. The method in accordance with claim 3, wherein the cosmetic composition is applied topically.

17. The method in accordance with claim 3, wherein the cosmetic composition comprises the peptide at a concentration of 0.0001%-0.05% (m/v).

18. The method in accordance with claim 3, wherein the subject in need thereof is a mammal.

19. The method in accordance with claim 18, wherein the mammal is a human.

20. The method in accordance with claim 6, wherein the cosmetic composition is applied by means of iontophoresis.

21. The method in accordance with claim 6, wherein the cosmetic composition is applied by subcutaneous injection.

22. The method in accordance with claim 6, wherein the cosmetic composition is applied topically.

23. The method in accordance with claim 6, wherein the cosmetic composition comprises the peptide at a concentration of 0.0001%-0.05% (m/v).

24. The method in accordance with claim 6, wherein the subject in need thereof is a mammal.

* * * * *

SEQUENCE LISTING

```
<160> NUMBER OF SEQ ID NOS: 16

<210> SEQ ID NO 1
<211> LENGTH: 594
<212> TYPE: PRT
```

<213> ORGANISM: Homo sapiens
<220> FEATURE:
<223> OTHER INFORMATION: Munc 18

<400> SEQUENCE: 1

```
Met Ala Pro Ile Gly Leu Lys Ala Val Gly Glu Lys Ile Met His
1               5                   10                  15

Asp Val Ile Lys Lys Val Lys Lys Lys Gly Glu Trp Lys Val Leu Val
            20                  25                  30

Val Asp Gln Leu Ser Met Arg Met Leu Ser Ser Cys Cys Lys Met Thr
        35                  40                  45

Asp Ile Met Thr Glu Gly Ile Thr Ile Val Glu Asp Ile Asn Lys Arg
    50                  55                  60

Arg Glu Pro Leu Pro Ser Leu Glu Ala Val Tyr Leu Ile Thr Pro Ser
65                  70                  75                  80

Glu Lys Ser Val His Ser Leu Ile Ser Asp Phe Lys Asp Pro Pro Thr
                85                  90                  95

Ala Lys Tyr Arg Ala Ala His Val Phe Phe Thr Asp Ser Cys Pro Asp
            100                 105                 110

Ala Leu Phe Asn Glu Leu Val Lys Ser Arg Ala Ala Lys Val Ile Lys
        115                 120                 125

Thr Leu Thr Glu Ile Asn Ile Ala Phe Leu Pro Tyr Glu Ser Gln Val
    130                 135                 140

Tyr Ser Leu Asp Ser Ala Asp Ser Phe Gln Ser Phe Tyr Ser Pro His
145                 150                 155                 160

Lys Ala Gln Met Lys Asn Pro Ile Leu Glu Arg Leu Ala Glu Gln Ile
                165                 170                 175

Ala Thr Leu Cys Ala Thr Leu Lys Glu Tyr Pro Ala Val Arg Tyr Arg
            180                 185                 190

Gly Glu Tyr Lys Asp Asn Ala Leu Leu Ala Gln Leu Ile Gln Asp Lys
        195                 200                 205

Leu Asp Ala Tyr Lys Ala Asp Asp Pro Thr Met Gly Glu Gly Pro Asp
    210                 215                 220

Lys Ala Arg Ser Gln Leu Leu Ile Leu Asp Arg Gly Phe Asp Pro Ser
225                 230                 235                 240

Ser Pro Val Leu His Glu Leu Thr Phe Gln Ala Met Ser Tyr Asp Leu
                245                 250                 255

Leu Pro Ile Glu Asn Asp Val Tyr Lys Tyr Glu Thr Ser Gly Ile Gly
            260                 265                 270

Glu Ala Arg Val Lys Glu Val Leu Leu Asp Glu Asp Asp Leu Trp
        275                 280                 285

Ile Ala Leu Arg His Lys His Ile Ala Glu Val Ser Gln Glu Val Thr
    290                 295                 300

Arg Ser Leu Lys Asp Phe Ser Ser Ser Lys Arg Met Asn Thr Gly Glu
305                 310                 315                 320

Lys Thr Thr Met Arg Asp Leu Ser Gln Met Leu Lys Lys Met Pro Gln
                325                 330                 335

Tyr Gln Lys Glu Leu Ser Lys Tyr Ser Thr His Leu His Leu Ala Glu
            340                 345                 350

Asp Cys Met Lys His Tyr Gln Gly Thr Val Asp Lys Leu Cys Arg Val
        355                 360                 365

Glu Gln Asp Leu Ala Met Gly Thr Asp Ala Glu Gly Glu Lys Ile Lys
    370                 375                 380

Asp Pro Met Arg Ala Ile Val Pro Ile Leu Leu Asp Ala Asn Val Ser
```

```
                385                 390                 395                 400
Thr Tyr Asp Lys Ile Arg Ile Ile Leu Leu Tyr Ile Phe Leu Lys Asn
                405                 410                 415

Gly Ile Thr Glu Glu Asn Leu Asn Lys Leu Ile Gln His Ala Gln Ile
            420                 425                 430

Pro Pro Glu Asp Ser Glu Ile Ile Thr Asn Met Ala His Leu Gly Val
        435                 440                 445

Pro Ile Val Thr Asp Ser Thr Leu Arg Arg Ser Lys Pro Glu Arg
    450                 455                 460

Lys Glu Arg Ile Ser Glu Gln Thr Tyr Gln Leu Ser Arg Trp Thr Pro
465                 470                 475                 480

Ile Ile Lys Asp Ile Met Glu Asp Thr Ile Glu Asp Lys Leu Asp Thr
                485                 490                 495

Lys His Tyr Pro Tyr Ile Ser Thr Arg Ser Ser Ala Ser Phe Ser Thr
                500                 505                 510

Thr Ala Val Ser Ala Arg Tyr Gly His Trp His Lys Asn Lys Ala Pro
            515                 520                 525

Gly Glu Tyr Arg Ser Gly Pro Arg Leu Ile Ile Phe Ile Leu Gly Gly
        530                 535                 540

Val Ser Leu Asn Glu Met Arg Cys Ala Tyr Glu Val Thr Gln Ala Asn
545                 550                 555                 560

Gly Lys Trp Glu Val Leu Ile Gly Ser Thr His Ile Leu Thr Pro Gln
                565                 570                 575

Lys Leu Leu Asp Thr Leu Lys Lys Leu Asn Lys Thr Asp Glu Glu Ile
                580                 585                 590

Ser Ser

<210> SEQ ID NO 2
<211> LENGTH: 288
<212> TYPE: PRT
<213> ORGANISM: Homo sapiens
<220> FEATURE:
<223> OTHER INFORMATION: Syntaxin-1

<400> SEQUENCE: 2

Met Lys Asp Arg Thr Gln Glu Leu Arg Thr Ala Lys Asp Ser Asp Asp
1               5                   10                  15

Asp Asp Asp Val Ala Val Thr Val Asp Arg Asp Arg Phe Met Asp Glu
            20                  25                  30

Phe Phe Glu Gln Val Glu Glu Ile Arg Gly Phe Ile Asp Lys Ile Ala
        35                  40                  45

Glu Asn Val Glu Glu Val Lys Arg Lys His Ser Ala Ile Leu Ala Ser
    50                  55                  60

Pro Asn Pro Asp Glu Lys Thr Lys Glu Glu Leu Glu Glu Leu Met Ser
65                  70                  75                  80

Asp Ile Lys Lys Thr Ala Asn Lys Val Arg Ser Lys Leu Lys Ser Ile
                85                  90                  95

Glu Gln Ser Ile Glu Gln Glu Glu Gly Leu Asn Arg Ser Ser Ala Asp
            100                 105                 110

Leu Arg Ile Arg Lys Thr Gln His Ser Thr Leu Ser Arg Lys Phe Val
        115                 120                 125

Glu Val Met Ser Glu Tyr Asn Ala Thr Gln Ser Asp Tyr Arg Glu Arg
    130                 135                 140

Cys Lys Gly Arg Ile Gln Arg Gln Leu Glu Ile Thr Gly Arg Thr Thr
145                 150                 155                 160
```

-continued

```
Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Asn Ser
        195                 200                 205

Ile Arg Glu Leu His Asp Met Phe Met Asp Met Ala Met Leu Val Glu
    210                 215                 220

Ser Gln Gly Glu Met Ile Asp Arg Ile Glu Tyr Asn Val Glu His Ala
225                 230                 235                 240

Val Asp Tyr Val Glu Arg Ala Val Ser Asp Thr Lys Lys Ala Val Lys
                245                 250                 255

Tyr Gln Ser Lys Ala Arg Arg Lys Lys Ile Met Ile Ile Cys Cys
                260                 265                 270

Val Ile Leu Gly Ile Val Ile Ala Ser Thr Val Gly Gly Ile Phe Ala
            275                 280                 285
```

<210> SEQ ID NO 3
<211> LENGTH: 6
<212> TYPE: PRT
<213> ORGANISM: Homo sapiens
<220> FEATURE:
<223> OTHER INFORMATION: Munc18 positions 46 to 51

<400> SEQUENCE: 3

Lys Met Thr Asp Ile Met
1               5

<210> SEQ ID NO 4
<211> LENGTH: 4
<212> TYPE: PRT
<213> ORGANISM: Homo sapiens
<220> FEATURE:
<223> OTHER INFORMATION: Munc18 positions 63 to 66

<400> SEQUENCE: 4

Lys Arg Arg Glu
1

<210> SEQ ID NO 5
<211> LENGTH: 6
<212> TYPE: PRT
<213> ORGANISM: Artificial Sequence
<220> FEATURE:
<223> OTHER INFORMATION: Artificially synthesized peptide

<400> SEQUENCE: 5

His Ile Leu Asp Met Trp
1               5

<210> SEQ ID NO 6
<211> LENGTH: 6
<212> TYPE: PRT
<213> ORGANISM: Artificial Sequence
<220> FEATURE:
<223> OTHER INFORMATION: Artificially synthesized sequence

<400> SEQUENCE: 6

His Ile Met Asp Phe Trp
1               5

<210> SEQ ID NO 7

```
<211> LENGTH: 6
<212> TYPE: PRT
<213> ORGANISM: Artificial Sequence
<220> FEATURE:
<223> OTHER INFORMATION: Artificially synthesized peptide

<400> SEQUENCE: 7

His Ile Leu Asp Trp Trp
1               5

<210> SEQ ID NO 8
<211> LENGTH: 6
<212> TYPE: PRT
<213> ORGANISM: Artificial Sequence
<220> FEATURE:
<223> OTHER INFORMATION: Artificially synthesized sequence

<400> SEQUENCE: 8

His Ala Leu Arg Phe Trp
1               5

<210> SEQ ID NO 9
<211> LENGTH: 6
<212> TYPE: PRT
<213> ORGANISM: Artificial Sequence
<220> FEATURE:
<223> OTHER INFORMATION: Artificially synthesized peptide

<400> SEQUENCE: 9

His Ile Met Asp Trp Trp
1               5

<210> SEQ ID NO 10
<211> LENGTH: 4
<212> TYPE: PRT
<213> ORGANISM: Artificial Sequence
<220> FEATURE:
<223> OTHER INFORMATION: Artificially synthesized peptide

<400> SEQUENCE: 10

Arg Arg Arg Phe
1

<210> SEQ ID NO 11
<211> LENGTH: 4
<212> TYPE: PRT
<213> ORGANISM: Artificial Sequence
<220> FEATURE:
<223> OTHER INFORMATION: Artificially synthesized peptide

<400> SEQUENCE: 11

Arg Met Arg Phe
1

<210> SEQ ID NO 12
<211> LENGTH: 8
<212> TYPE: PRT
<213> ORGANISM: Homo sapiens
<220> FEATURE:
<223> OTHER INFORMATION: Munc18 positions 59 to 66

<400> SEQUENCE: 12

Glu Asp Ile Asn Lys Arg Arg Glu
1               5

<210> SEQ ID NO 13
<211> LENGTH: 8
```

```
<212> TYPE: PRT
<213> ORGANISM: Artificial Sequence
<220> FEATURE:
<223> OTHER INFORMATION: Artificially synthesized peptide

<400> SEQUENCE: 13

Glu Arg Ile Asn Lys Arg Arg Trp
1               5

<210> SEQ ID NO 14
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 14

Glu Arg Ile Asn Lys Met Arg Tyr
1               5

<210> SEQ ID NO 15
<211> LENGTH: 6
<212> TYPE: PRT
<213> ORGANISM: Artificial Sequence
<220> FEATURE:
<223> OTHER INFORMATION: Artificially synthesized sequence
<220> FEATURE:
<221> NAME/KEY: VARIANT
<222> LOCATION: 2
<223> OTHER INFORMATION: Xaa is selected from the group Gly, Ala, Val,
      Leu, Met and Ile
<220> FEATURE:
<221> NAME/KEY: VARIANT
<222> LOCATION: 3
<223> OTHER INFORMATION: Xaa is selected from the group Gly, Ala, Val,
      Leu, Met and Ile
<220> FEATURE:
<221> NAME/KEY: VARIANT
<222> LOCATION: 4
<223> OTHER INFORMATION: Xaa is selected from the group of Lys, Arg,
      His, Asp and Glu
<220> FEATURE:
<221> NAME/KEY: VARIANT
<222> LOCATION: 5
<223> OTHER INFORMATION: Xaa is selected from the group of Met, Phe, Tyr
      and Trp

<400> SEQUENCE: 15

His Xaa Xaa Xaa Xaa Trp
1               5

<210> SEQ ID NO 16
<211> LENGTH: 4
<212> TYPE: PRT
<213> ORGANISM: Artificial Sequence
<220> FEATURE:
<223> OTHER INFORMATION: Artificially synthesized peptide
<220> FEATURE:
<221> NAME/KEY: VARIANT
<222> LOCATION: 1
<223> OTHER INFORMATION: Xaa is selected from the group of Lys, Arg and
      His
<220> FEATURE:
<221> NAME/KEY: VARIANT
<222> LOCATION: 2
<223> OTHER INFORMATION: Xaa is selected from the group Ala, Arg, Asn,
      Asp, Cys, Glu, Gln, Gly, His, Ile, Leu, Lys, Met, Phe, Pro, Ser,
      Thr, Trp, Tyr, Val, citrulline, ornithine, sarcosine, desmosine,
      norvaline, 4-aminobutyric acid, 2-aminobutyric acid,
      2-aminoisobutyric acid, 6-aminohexanoic acid, 1-naphthylalanine,
      2-naphthylalanine, 2-aminobenzoic acid, 4 aminobenzoic acid,
      4-chlorophenylalanine, 2,3-diaminopropionic acid, 2,4
      diaminobutyric acid, cycloserine, carnitine, cysteine,
```

```
        penicillamine, pyroglutamic acid, thienylalanine, hydroxyproline,
        allo-isoleucine, allo-threonine, isonipecotic acid, isoserine,
        phenylglycine, statin, beta-alanine, norleucine, N-methylamino
        acids, alpha-amino acids and beta-amino acids.
<220> FEATURE:
<221> NAME/KEY: VARIANT
<222> LOCATION: 3
<223> OTHER INFORMATION: Xaa is selected from the group of Lys, Arg and
      His
<220> FEATURE:
<221> NAME/KEY: VARIANT
<222> LOCATION: 4
<223> OTHER INFORMATION: Xaa is selected from the group of Phe, Tyr and
      Trp

<400> SEQUENCE: 16

Xaa Xaa Xaa Xaa
1
```